US011337944B2

(12) United States Patent
Acevedo-Duncan et al.

(10) Patent No.: US 11,337,944 B2
(45) Date of Patent: May 24, 2022

(54) METHOD OF TREATING COLORECTAL CANCERS USING A PKC INHIBITOR

(71) Applicants: UNIVERSITY OF SOUTH FLORIDA, Tampa, FL (US); UNIVERSITY OF FLORIDA RESEARCH FOUNDATION, INC., Gainesville, FL (US)

(72) Inventors: Mildred Acevedo-Duncan, Plant City, FL (US); Anisul Islam, Tampa, FL (US); David A. Ostrov, Gainesville, FL (US)

(73) Assignees: UNIVERSITY OF SOUTH FLORIDA, Tampa, FL (US); UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 23 days.

(21) Appl. No.: 15/643,117

(22) Filed: Jul. 6, 2017

(65) Prior Publication Data
US 2018/0008564 A1 Jan. 11, 2018

Related U.S. Application Data

(60) Provisional application No. 62/359,496, filed on Jul. 7, 2016.

(51) Int. Cl.
*A61K 31/185* (2006.01)
*C12Q 1/6886* (2018.01)
*G01N 33/50* (2006.01)
*A61K 31/675* (2006.01)
*A61K 31/122* (2006.01)
*C12Q 1/48* (2006.01)

(52) U.S. Cl.
CPC .......... *A61K 31/185* (2013.01); *A61K 31/122* (2013.01); *A61K 31/675* (2013.01); *C12Q 1/485* (2013.01); *C12Q 1/6886* (2013.01); *G01N 33/5011* (2013.01); *C12Q 2600/106* (2013.01); *C12Q 2600/158* (2013.01); *G01N 2333/91215* (2013.01); *G01N 2800/52* (2013.01)

(58) Field of Classification Search
CPC .......... G01N 33/5011; G01N 2800/52; G01N 2333/91215; C12Q 2600/106; C12Q 1/6886; C12Q 1/485; C12Q 2600/158; A61K 31/185; A61K 31/675; A61K 31/122
See application file for complete search history.

(56) References Cited

U.S. PATENT DOCUMENTS 9,301,965 B2 * 4/2016 Acevedo-Duncan ....................... A61K 31/675
2015/0366883 A1 * 12/2015 Acevedo-Duncan ....................... A61K 31/675
514/94

OTHER PUBLICATIONS

Lee et al. Biochemical and Biophysical Research Communications 424 (2012) 321-326. (Year: 2012).*
www.cancer.gov website, Cancer Types, Gastrointestinal Carcinoid Tumors, https://www.cancer.gov/types/gi-carcinoid-tumors, accessed Jan. 21, 2018. (Year: 2018).*
Allred, D. C. et al., "Prognostic and Predictive Factors in Breast Cancer by Immunohistochemical Analysis," *Modern Pathology*, 1998, 11 (2):155-168, The United States and Canadian Academy of Pathology, Inc.
Bradford, M. M., "A Rapid and Sensitive Method for the Quantitation of Microgram Quantities of Protein Utilizing the Principle of Protein-Dye Binding," *Analytical Biochemistry*, 1976, 72:248-254, Academic Press, Inc.
Diaz-Meco, M. T. et al., "Lambda-Interacting Protein, a Novel Protein That Specifically Interacts with the Zinc Finger Domain of the Atypical Protein Kinase C Isotype λ/i and Stimulates Its Kinase Activity In Vitro and In Vivo," *Molecular and Cellular Biology*, Jan. 1996, 16(1): 105-114, American Society for Microbiology.
Eder, A. M. et al., "Atypical PKCi contributes to poor prognosis through loss of apical-basal polarity of Cyclin E overexpression in ovarian cancer," *PNAS*, Aug. 30, 2005, 102(35):12519-12524, The National Academy of Sciences of the USA.
Housey, G. M. et al., "Overproduction of Protein Kinase C Causes Disordered Growth Control in Rat Fibroblasts," *Cell*, Feb. 12, 1988, 52:343-354, Cell Press.
Kamata, T. et al., "Reduced protein kinase C activity in a ras-resistant cell line derived from Ki-MSV transformed cells," *Oncogene*, 1987, 1:37-46, The Macmillan Press Ltd.
Laemmli, U. K., "Cleavage of Structural Proteins during the Assembly of the Head of Bacteriophage T4," *Nature*, Aug. 15, 1970, 227:680-658, Nature Publishing Group.
Mizuguchi, J. et al., "Increased Degradation of Protein Kinase C without Diminution of mRNA Level After Treatment of WEHI-231 B Lymphoma Cells with Phorbol Esters," *Biochemical and Biophysical Research Communications*, Sep. 30, 1988, 155(3): 1311-1317, Academic Press, Inc.
Persons, D. A. et al., "Altered Growth Regulation and Enhanced Tumorigenicity of NIH 3T3 Fibroblasts Transfected with Protein Kinase C—I cDNA," *Cell*, Feb. 12, 1988, 52:447-458, Cell Press.
Regala, R. P. et al., "Atypical Protein Kinase Ci Plays a Critical Role in Human Lung Cancer Cell Growth and Tumorigenicity," *The Journal of Biological Chemistry*, Sep. 2, 2005, 280(35):31109-31115, The American Society for Biochemistry and Molecular Biology, Inc.

(Continued)

*Primary Examiner* — James D. Anderson
*Assistant Examiner* — William Y Lee
(74) *Attorney, Agent, or Firm* — Quarles & Brady LLP

(57) ABSTRACT

The subject invention pertains to methods of treating colorectal cancer by administering an atypical PKC inhibitor. The inhibitors of aPKC useful in the methods of the instant invention include ACPD, ICA-1, DNDA and ζ-Stat. Also provided are methods of measuring the susceptibility of colon cancer cells of a subject to inhibitors of aPKCs.

11 Claims, 12 Drawing Sheets

(56) References Cited

OTHER PUBLICATIONS

Towbin, H. et al., "Electrophoretic transfer of proteins from polyacrylamide gels to nitrocellulose sheets: Procedure and some applications," *Proc. Natl. Acad. Sci., Biochemistry*, Sep. 1979, 76(9):4350-4354.

Weyman, C. M. et al., Partial Down-Regulation of Protein Kinase C in C3H 10T½ Mouse Fibroblasts Transfected with the Human Ha-ras Oncogene[1], *Cancer Research*, Nov. 15, 1998, 48:6535-6541, American Association for Cancer Research.

"Colorectal Cancer—Patient Version", Web Page, < https://www.cancer.gov/types/colorectal >, 4 Pages, Jun. 14, 2018, retrieved from Internet Archive Wayback Machine < https://web.archive.orq/web/20180614184937/https://www.cancer.gov/types/colorectal >, on Jul. 24, 2018.

Alkan, S. et al., "Survival Role of Protein Kinase C (PKC) in Chronic Lymphocytic Leukemia and Determination of Isoform Expression Pattern and Genes Altered by PKC Inhibition," *American Journal of Hematology*, 2005, 79:97-106, Wiley-Liss, Inc.

McCray, A. N. et al., The Interruption of PKC-t Signaling and TRAIL Combination Therapy Against Glioblastoma Cells, *Neurochem Res*, 2014, 39:1691-1701, Springer Science+Business Media New York.

Brodbeck, D. et al., "A Human Protein Kinase By with Regulatory Phosphorylation Sites in the Activation Loop and in the C-terminal Hydrophobic Domain*," *The Journal of Biological Chemistry*, 1999, 274(14):9133-9136, The American Society for Biochemistry and Molecular Biology, Inc.

Calvert, P. M. et al., "The Genetics of Colorectal Cancer," *Annals of Internal Medicine*, Oct. 1, 2002, 137(7):603-612, American College of Physicians-American Society of Internal Medicine.

Castagna, M. et al., "Direct Activation of Calcium-activated, Phospholipid-dependent Protein Kinase by Tumor-promoting Phorbol Esters*," *The Journal of Biological Chemistry*, Jul. 10, 1982, 257(13):7847-7851.

Chan, C. et al., "Deciphering the transcription complex critical for RhoA gene expression and cancer metastasis," *Nat Cell Biol.*, May 2010, 12(5):1-29.

Chan, C. et al., "Regulation of Skp2 Expression and Activity and Its Role in Cancer Progression," *The Scientific World Journal*, 2010, 10:1001-1015, TheScientificWorld.

Chen, X. et al., "Constitutively active Akt is an important regulator of TRAIL sensitivity in prostate cancer," *Oncogene*, 2001, 20:6073-6083, Nature Publishing Group.

Cheng, J. Q. et al., "AKT2, a putative oncogene encoding a member of a subfamily of protein-serine/threonine kinases, is amplified in human ovarian carcinomas," *Proc. Natl. Acad. Sci.*, Oct. 1992, 89:9267-9271.

Couldwell, W. et al., "Inhibition of growth of established human glioma cell lines by modulators of the protein kinase-C system," Oct. 1990, *J Neurosurg*, 73:594-600.

Crews, C. M. et al., "The Primary Structure of MEK, a Protein Kinase That Phosphorylates the ERK Gene Product," *Science*, Oct. 16, 1992, 258:478-480.

Datta, S. R. et al., "14-3-3 Proteins and Survival Kinases Cooperate to Inactivate BAD by BH3 Domain Phosphorylation," *Molecular Cell*, Jul. 2000, 6:41-51, Cell Press.

Elghazi, L. et al., "Emerging role of protein kinase B/Akt signaling in pancreatic ß-cell mass and function*," *The International Journal of Biochemistry & Cell Biology*, 2006, 38:689-695, Elsevier Ltd.

Vara, J. A. F. et al., "PI3K/Akt signaling pathway and cancer*," *Cancer Treatment Reviews*, 2004, 30:193-204, 2003 Elsevier Ltd.

Gao, T. et al., "The Carboxyl Terminus of Protein Kinase C Provides a Switch to Regulate Its Interaction with the Phosphoinositide-dependent Kinase, PDK-1*," *The Journal of Biological Chemistry*, Jun. 1, 2001, 276(22):19588-19596, The American Society for Biochemistry and Molecular Biology, Inc.

Hajduch, E. et al., "Protein kinase B (PKB/Akt)—a key regulator of glucose transport?," *FEBS Letters*, 2001, 492:199-203, Federation of European Biochemical Societies.

Hirai, T. et al., "Protein Kinase Cζ: Activation Mechanisms and Cellular Functions," *J. Biochem.*, 2003, 133:1-7, The Japanese Biochemical Society.

Hirai, I. et al., "Survival-factor-induced phosphorylation of Bad results in its dissociation from Bcl-$x_L$ but not Bcl-2," *Biochem. J.*, 2001, 359:345-352, Biochemical Society.

Huang, D. C. S. et al., "BH3-Only Proteins-Essential Initiators of Apoptotic Cell Death," *Cell*, Dec. 8, 2000, 103:839-842, Cell Press.

Jemal, A. et al., "Global Cancer Statistics," *CA Cancer J Clin*, 2011, 61:69-90, American Cancer Society, Inc.

Ji, P. et al., "An Rb-Skp2-p27 Pathway Mediates Acute Cell Cycle Inhibition by Rb and Is Retained in a Partial-Penetrance Rb Mutant," *Molecular Cell*, Oct. 8, 2004, 16:47-58, Cell Press.

Jin, Z. et al., "Tobacco-specific Nitrosamine 4-(Methylnitrosamino)-1-(3-pyridyl)-1-butanone Promotes Functional Cooperation of Bc12 and c-Myc through Phosphorylation in Regulating Cell Survival and Proliferation*," *The Journal of Biological Chemistry*, Sep. 17, 2004, 279(38):40209-40219, The American Society for Biochemistry and Molecular Biology, Inc.

Johannes, F. et al., "PKCu Is a Novel, Atypical Member of the Protein Kinase C Family*," *The Journal of Biological Chemistry*, Feb. 25, 1994, 269(8):6140-6148, The American Society for Biochemistry and Molecular Biology, Inc.

Jones, P. F. et al., "Molecular cloning of a second form of rac protein kinase," *Cell Regulation*, Dec. 1991, 2:1001-1009, The American Society for Cell Biology.

Kandasamy, K. et al., "Role of the Phosphatidylinositol 3'-Kinase/PTEN/Akt Kinase Pathway in Tumor Necrosis Factor-related Apoptosis-inducing Ligand-induced Apoptosis in Non-Small Cell Lung Cancer Cells," *Cancer Research*, Sep. 1, 2002, 62:4929-4937, American Association for Cancer Research.

Kishimoto, A. et al., "Activation of Calcium and Phospholipid-dependent Protein Kinase by Diacylglycerol, Its Possible Relation to Phosphatidylinositol Turnover*," *The Journal of Biological Chemistry*, Mar. 25, 1980, 255(6):2273-2276.

Kitagawa, M. et al., "Skp2 Suppresses p53-Dependent Apoptosis by Inhibiting p300," *Molecular Cell*, Feb. 1, 2008, 29:217-231, Elsevier Inc.

Lavoie, J. N. et al., "Cyclin D1 Expression Is Regulated Positively by the p42/p44$^{MAPK}$ and Negatively by the p38/HOG$^{MAPK}$ Pathway*," *The Journal of Biological Chemistry*, Aug. 23, 1996, 271(34):20608-20616, The American Society for Biochemistry and Molecular Biology, Inc.

Lewis, T. S. et al., "Signal Transduction through MAP Kinase Cascades," *Advances in Cancer Research*, 1998, pp. 49-139, Academic Press.

Lin, B. et al., "Conversion of Bcl-2 from Protector to Killer by Interaction with Nuclear Orphan Receptor Nur77/TR3," *Cell*, Feb. 20, 2004, 116:527-540, Cell Press.

Mahadev, K. et al., "Integration of multiple downstream signals determines the net effect of insulin on MAP kinase vs. PI 3'-kinase activation: potential role of insulin-stimulated $H_2O_2$," *Cellular Signalling*, 2004, 16:323-331, 2003 Elsevier Inc.

Martin, G. S., "Cell signaling and cancer," *Cancer Cell*, Sep. 2003, 4:167-174, Cell Press.

Moscat, J. et al., "Cell Signaling and Function Organized by PB1 Domain Interactions," *Molecular cell*, Sep. 1, 2006, 23:631-640, Elsevier Inc.

Moscat, J. et al., "PKCζ at the crossroad of NF-$_κ$B and Jak1/Stat6 signaling pathways," *Cell Death and Differentiation*, 2006, 13:702-711, Nature Publishing Group.

Murray, N. R. et al., "Protein kinase Ct is required for Ras transformation and colon carcinogenesis in vivo," *The Journal of Cell Biology*, Mar. 15, 2004, 164(6):797-802, The Rockefeller University Press.

Nelson, et al., "Regulation of the Cell Cycle by Protein Kinases," *Lehninger Principles of Biochemistry*, p. 469.

(56) References Cited

OTHER PUBLICATIONS

Newton, A. C., "Protein Kinase C: Structure, Function, and Regulation*," *The Journal of Biological Chemistry*, Dec. 1, 1995, 270(48):28495-28498, The American Society for Biochemistry and Molecular Biology, Inc.

Newton, A. C., "Protein Kinase C: Structural and Spatial Regulation by Phosphorylation, Cofactors, and Macromolecular Interactions," *Chem. Rev.*, 2001, 101:2353-2364, American Chemical Society.

Nicholson, K. M. et al., "The protein kinase B/Akt signalling pathway in human malignancy," *Cellular Signalling*, 2002, 14:381-395, Elsevier Science, Inc.

Nishizuka, Y., "Intracellular Signalling by Hydrolysis of Phospholipids and Activation of Protein Kinase C," *Science*, Oct. 23, 1992, 258(5082):607-614, American Association for the Advancement of Science.

Palmer, R. H. et al., "Cloning and expression patterns of two members of a novel protein-kinase-C-related kinase family," *Eur. J. Biochem.*, 1995, 227:344-351, FEBS.

Rodriguez, S. et al., "The SKP2 E3 ligase regulates basal homeostasis and stress-induced regeneration of HSCs," *Blood*, Jun. 16, 2011, 117(24):6509-6519, The American Society of Hematology.

Santen, R. J. et al., "The role of mitogen-activated protein (MAP) kinase in breast cancer," *Journal of Steroid Biochemistry & Molecular Biology*, 2002, 80:239-256, Elsevier Science Ltd.

Sato, S. et al., "Involvement of 3-Phosphoinositide-dependent Protein Kinase-1 in the MEK/MAPK Signal Transduction Pathway*," *The Journal of Biological Chemistry*, Aug. 6, 2004, 279(32):33759-33767, The American Society for Biochemistry and Molecular Biology, Inc.

Sebolt-Leopold, J. S. et al., "Development of anticancer drugs targeting the MAP kinase pathway," *Oncogene*, 2000, 19:6594-6599, Macmillan Publishers Ltd.

Selbie, L. A. et al., "Molecular Cloning and Characterization for PKCt, an Atypical Isoform of Protein Kinase C Derived from Insulin-secreting Cells*," *The Journal of Biological Chemistry*, Nov. 15, 1993, 268(32):24296-24302, The American Society for Biochemistry and Molecular Biology, Inc.

Smalley, K. S. M. "A Pivotal Role for ERK in the Oncogenic Behaviour of Malignant Melanoma?" *Int. J. Cancer*, 2003, 104:527-532, Wiley-Liss, Inc.

Tait, S. W. G. et al., "Mitochondria and cell death: outer membrane permeabilization and beyond," *Nature Reviews, Molecular Cell Biology*, Sep. 2010, 11: 621-632, Macmillan Publishers Limited.

Suzuki, M. et al., "Structure of Bax: Coregulation of Dimer Formation and Intracellular Localization," *Cell*, Nov. 10, 2000, 103:645-654, Cell Press.

Tan, Y. et al., "BAD Ser-155 Phosphorylation Regulates BAD/Bcl-XL Interaction and Cell Survival*," *The Journal of Biological Chemistry*, Aug. 18, 2000, 275(33):25865-25869, The American Society for Biochemistry and Molecular Biology, Inc.

Testa, J. R. et al., "AKT plays a central role in tumorigenesis," *PNAS*, Sep. 25, 2001, 98(20):10983-10985.

Wang, Q. et al., "Regulation of TRAIL Expression by the Phosphatidylinositol 3-Kinase/Akt/GSK-3 Pathway in Human Colon Cancer Cells," *The Journal of Biological Chemistry*, Sep. 27, 2002, 277(39):36602-36610, The American Society for Biochemistry and Molecular Biology, Inc.

Wang, Z. et al., "Skp2: A novel potential therapeutic target for prostate cancer," *Biochimica et Biophysica Acta*, 2012, 1825:11-17, 2011 Elsevier B.V.

Wang, H. et al., "Skp2 is required for survival of aberrantly proliferating Rb1-deficient cells and for tumorigenesis in Rb1$^{+/-}$mice," *Nat. Genet.*, Jan. 2010, 42(1):83-88.

Wheeler, D. L. et al., "Protein Kinase C Epsilon Signals Ultraviolet Light-induced Cutaneous Damage and Development of Squamous Cell Carcinoma Possibly Through Induction of Specific Cytokines in a Paracrine Mechanism," *Photochemistry and Photobiology*, 2005, 81 (1):9-18, American Society for Photobiology.

Win, H. Y. et al., "Role of protein kinase C-iota in transformed non-malignant RWPE-1 cells and androgen-independent prostate carcinoma DU-145 cells," *Cell Prolif.*, 2009, 42:182-194, Blackwell Publishing Ltd.

Yuan, X. et al., " PTEN sensitizes prostate cancer cells to death receptor-mediated and drug-induced apoptosis through a FADD-dependent pathway," *Oncogene*, 2002, 21:319-327, Nature Publishing Group.

"Lifetime Risk of Developing or Dying From Cancer", Web Page <http://www.cancer.org/cancer/cancerbasics/lifetime-probability-of-developing-or-dving-from-cancer>, 12 pages, Dec. 9, 2010, retrieved from Internet Archive Wayback Machine < https://web.archive.org/web/20101209201404/http://www.cancer.org/cancer/cancerbasics/lifetime-probability-of-developing-or-dying-from-cancer >, on Jul. 19, 2018.

"Types of colorectal cancer", Web Page < http://www.cancercenter.com/colorectal-cancer/types >, 3 pages, Dec. 9, 2016, retrieved from Internet Archive Wayback Machine < https://web.archive.org/web/20161209145911/http://www.cancercenter.com/colorectal-cancer/types >, on Jul. 19, 2018.

"What You Need to Know About Colorectal Cancer", Web Page < http://www.webmd.com/colorectal-cancer/ss/slideshow-colorectal-cancer-overview >, 46 pages, Apr. 11, 2016, retrieved from Internet Archive Wayback Machine < https://web.archive.org/web/20160411160611/https://www.webmd.com/colorectal-cancer/ss/slideshow-colorectal-cancer-overview >, on Jul. 19, 2018.

Islam, S. M. A. et al., "The role of Protein Kinase C- ζ (PKC- ζ) in Colorectal Cancer Cell growth and Proliferation (A study of a specific PKC- ζ inhibitor, ζ-Stat)," University of South Florida, Tampa, FL.

Apostolatos, A. H. et al., "Abstract 3470: Atipical protein kinase C inhibition in prostate cancer cells: A study of ICA-1 and ACPD," *Endocrinology*, Aug. 1, 2015, American Association for Cancer Research, Proceedings: AACR 106$^{th}$ Annual Meeting 2015; Apr. 18-22, 2015; Philadelphia, PA.

* cited by examiner

METHOD OF TREATING COLORECTAL CANCERS USING A PKC INHIBITOR

CROSS-REFERENCE TO RELATED APPLICATION

This application claims the benefit of U.S. Provisional Application Ser. No. 62/359,496, filed Jul. 7, 2016, the disclosure of which is hereby incorporated by reference in its entirety, including all figures, tables and drawings.

FIELD OF THE INVENTION

This invention relates to treating cancer with inhibitors of atypical protein kinase C. Specifically, the invention describes methods of treating colorectal cancers using a protein kinase C (PKC) inhibitor such as 2-acetyl-1,3-cyclopentanedione (ACPD), [4-(5-amino-4-carbamoylimidazol-1-yl)-2,3-dihydroxycyclopentyl] methyl dihydrogen phosphate (ICA-1), 3,4, diamino-2,7-naphthalene disulfonic acid (DNDA), or 8-hydroxy-1, 3,6-naphthalenetrisulfonic acid (ζ-Stat).

BACKGROUND OF THE INVENTION

Colorectal cancer is one of the most common and lethal cancers in the world. Globally, the incidence of colon cancer varies over 10-fold [1]. It is the second leading cause of cancer-related mortality in the United States. Over the past decade, colorectal cancer incidence and mortality rates have decreased in all racial/ethnic populations except American Indians/Alaska Natives. According to the US National Cancer Institute's Surveillance Epidemiology and End Results (SEER) database, the risk of developing colorectal cancer is 1 in 21 (4.69%) in man adn 1 in 23 (4.35%) in women based on the incidence and mortality rate from 2010 to 2012. Also, the risk of dying from colorectal cancer is 1 in 50 (1.99%) in male and 1.55 (1.81%) in females [61]. Men and women have similar incidence rates through age 39; at and above age 40, rates are higher in men [2].

Colorectal cancer or Colorectal adenocarcinoma or CRC is the development of cancer in the colon or rectum due to the abnormal growth of cells that have the ability to invade or spread to other parts of the body [4]. Colorectal cancer often begins as a growth called a polyp, which may form on the inner wall of the colon or rectum (FIG. 1). Over time, polyps may become malignant [2]. Colorectal cancers are mostly adenocarcinomas (cancers that begin in cells that make and release mucus and other fluids. Other colorectal cancers can include: Gastrointestinal carcinoid tumor, slow-growing cancer that forms in the neuroendocrine cell (a nerve cell that also creates hormones) in the lining of the gastrointestinal tract; Gastrointestinal stromal tumor, also known as GISTs, this is a rare type of colorectal cancer that starts in a special cell found in the lining of the gastrointestinal (GI) tract called interstitial cells of Cajal (ICCs); Primary colorectal lymphoma, a type of non-Hodgkin lymphoma (NHL), lymphomas are cancers that develop in the lymphatic system from cells called lymphocytes; Leiomyosarcoma, another form of sarcoma, leiomyosarcomas essentially means cancer of smooth muscle; Melanoma, though most commonly associated with the skin, melanomas can occur anywhere, including the colon or rectum and Squamous cell carcinoma, cancer of the squamous cells of the upper esophagus and the end of the anus [62]. Based on the depth and severity of the disease progress, CRC can be divided into five stages: stage-0: only innermost lining of the colon or rectum has been affected, Stage-I: cancer grown up to the muscle layer, Stage II: Outermost layer of the colon has been affected, Stage III: the disease has spread into one or more lymph nodes, Stage-IV: cancer becomes malignant and metastasized to other part of the body such as liver, lungs or bone. 9 (FIG. 2) [63]. The development of colorectal carcinogenesis is a complex multistep process accompanied by the disruption of the intestinal epithelial-cell growth, proliferation, differentiation, apoptosis, and survival mechanism [3]. The etiological understanding of this life threatening disease is still unknown. Tumor progression is usually acquired by a number of characteristic alterations. These alterations can include the uncontrolled proliferation of cells independently of extracellular promoting or inhibitory signals, invasiveness to nearby tissues and metastasize to distant sites, elicitation of an angiogenic response, and obstacles in the mechanisms that limit cell proliferation, such as apoptosis and replicative senescence. These properties reflect alterations in the cellular signaling pathways. Many proteins that are important component of the cell signaling pathways are currently under investigation as possible target for cancer therapy [5]. One of those most important proteins that is involved in controlling crucial cellular signal transduction pathways is Protein Kinase C (known as PKC) [6].

Protein kinase C (PKC) is a family of isozymes, also known as phospholipid dependent serine/threonine kinases that transduce signals and control other proteins through phosphorylation. PKC is a family of fourteen known isozymes which are found in varying ratios in the cytostolic and membrane fraction of cells depending on the type of tissue and its physiological state. (Nishizuka, Y. Intracellular signally by hydrolysis of phospholipids and activation of protein kinase C. Science. (1992); 258: 607-614.) The PKCs sit at the cross roads of many transmembrane signal transduction pathways that can be triggered by various external and internal stimuli [8]. PKCs are associated with many cell functions including survival, proliferation, motility and apoptosis [9]. The activation of some PKCs require calcium, lipid metabolites such as Diacylglycerol (DAG), co-factors like phosphotidyl serine (PS) and secondary messengers (phorbol esters) [10,11].

PKC isozymes can be classified into three groups based on their structure and requirements (i.e. activators and co-activators) for activation. Group I includes conventional isozymes: cPKC-α, cPKC-β1, cPKC-β11, and cPKC-γ all of which are activated by calcium and Diacylglycerol (DAG). Novel isozymes in group II (nPKC-ε, nPKC-δ, nPKC-η and PKC-θ) are Ca2+ independent but require Diacylglycerol (DAG) and phospholipids to get activated. Group III includes the atypical PKCs (aPKC-ι, aPKC-ζ, aPKC-ζ11, aPKC-μ (protein kinase D) and aPKC-ν) which are insensitive to both diacylglycerol and calcium and neither bind to nor are activated by phorbol esters. PKC Lamda (λ) in mouse is equivalent to aPKC-ι in human. Another distant member of the PKC family is PKC related kinases (PRK 1-3), known as PKN [13].

PKC is a single polypeptide consisting of a regulatory N terminal (approximately 20-40 kDa) and a catalytic C terminal (approximately 45 kDa) (FIG. 1). All PKC isozymes have similar highly conserved catalytic domain, also known as kinase domain consisting of motifs for ATP/substrate binding and catalysis but differ in their regulatory domain that maintain the enzyme in an inactive form. The regulatory domain also has a pseudosubstrate region (a sequence that has Alanin in place of Serine/Threonine phosphogroup acceptor which otherwise mimic a PKC substrate) and two discrete membrane targeting modules, termed C1 and C2. Conventional PKCs have a C1 domain termed as C1A and C1B (each consisting of 6 cysteine and 2 histidine residues coordinate with two Zn2+) that serve as a binding site for tumor promoting phorbol ester and diacylglycerol (DAG), C2 domain that binds anionic phospholipid in a calcium dependent manner. Novel PKCs also have twin C1 domain but they lack critical calcium coordinating acidic residues even though they have a so called C2 domain. The activation mechanism of PKCs involves two steps, first release of pseudosubstrate and, second, phosphorylation of kinase domain [15].

Atypical PKC:

Atypical PKC (aPKC), PKC-ι and PKC-ζ are different from other PKC isozymes both structurally and functionally. PKC-ι and PKC-ζ are the human homologs of the mouse PKC-λ (lamda). PKC-ι and PKC-ζ have significantly different structures from the other two groups of PKCs. Like other PKCs, the aPKCs also have a regulatory domain and a catalytic domain, the N-terminus of regulatory has a protein-protein interacting PB1 (Phox and Bem 1) domain (required for interaction with other PB1 containing scaffolding proteins such as p62, partitioning defective-6, called PAR-6 & MEK-5), a pseudo-substrate sequence, an atypical C1 domain of single Cysteine rich zinc finger motif that can bind Phosphatidylinositol 3,4,5 triphosphate (PIP3) and ceramide but the key residue that maintain the C2 fold is absent in this category of PKC isozyme and the C-terminus contains a kinase domain (FIG. 2). The structural differences make them insensitive to $Ca^{2+}$, DAG and phorbol ester. Atypical PKC activity is regulated primarily by protein-protein interactions and phosphorylation by phosphoinositide-dependent kinase-1, also called PDK-1 and Protein Kinase B, also known as PKB/Akt (PDK-1 and Akt, isozymes of AGC kinase family that contains a pleckstrin homology (PH domain), which can carry PIP-3 required for enzyme activity) [39,40]. The primary structure of atypical PKCs indicates that they are 72% homologues in regulatory and 84% homologues in catalytic domain. Atypical PKCs are of particular interest because of their involvement in cell cycle disruption, cell survival, apoptosis and tumor progression [14].

Role of PKC in Cell Malignancies:

PKC regulates cellular functions, metabolism and proliferation by phosphorylating proteins in response to transmembrane signals from hormones, growth factors, neurotransmitters, and pharmacological agents. Activation of PKC by various agonists (including radiation) results in altered transcription of a considerable number of genes. PKC is the major receptor for tumor promoting phorbol esters, but the extent of PKC involvement in cellular malignancy is not clearly defined. Various studies indicate that increased tumorigenicity results from dysregulation of PKC activity, or changes in PKC concentration, or both (Persons D A, Wilkison W O, Bell R M. et al. Altered growth regulation and enhanced tumorigenicity of NIH 3T3 fibroblasts transfected with protein kinase C-I DNA. Cell 1988; 52:447-458; Housey G M, Johnson M D, Hsiao W L M, et al. Overproduction of protein kinase C causes disordered growth control in rat fibroblasts. Cell 1988; 52:343-354; Kamata T, Sullivan N F and Wooten M W. Reduced protein kinase C activity in a ras-resistant cell line derived from Ki-MSV transformed cells. Oncogene 1987; 1:37-46; Weyman C M, Taparowsky E J, Wolfson M, et al. Partial down-regulation of protein kinase C in C3H10t1/2 mouse fibroblasts transfected with the human Ha-ras oncogene. Cancer Res. 1988; 48: 6535-6541; Mizuguhi J, Makabayashi H, Yoshida Y. Et al. Increased degradation of protein kinase C without diminution of mRNA level after treatment of WEHI-231 B lymphoma cells with phorbol esters. Biochem. Biophy. Res. Commun. 1988; 155:1311-1317).

PKC's are involved in normal cell functioning but when they are disrupted they can cause many adverse effects. PKC's have been discovered to play a role in tumor growth and formation when the levels of PKC are vastly altered.

PKC-ι is a member of the PKC family located in chromosome 3 at 3q26.2 and has been shown to be a human oncogene. There is an expanding body of knowledge regarding the status of atypical PKC-ι which does not contain a Ca 2+-binding region, has one zinc finger-like motif and is the human homolog of the mouse PKC-λ. (Bradford M M. A rapid and sensitive method for the quantitation of microgram quantities of protein utilizing the principle of protein-dye binding. Anal. Biochem. 1976; 72, 248-254).

PKC's have been shown to be overexpressed in a variety of cancers including ovarian, lung, head, neck, and prostate. Elder et al. provided evidence for the role of PKC-ι in cell proliferation by showing that increased PKC-ι protein levels were associated with increased cyclin E protein expression and proliferation of ovarian cancers (Laemmli UK. Cleavage of structural proteins during the assembly of the head of bacteriophage T4. Nature 1970; 337:680-685). In non-serous ovarian cancers they demonstrated that increased PKC-ι protein levels markedly decreased overall survival. Work from Field's laboratory indicated that PKC-ι is critical for non-small cell lung cancer proliferation in-vivo by activation of Rac1/Pak/Mek1,2/Erk1,2 signaling pathway which has been implicated in tumor cell proliferation and concluded that PKC-ι is an oncogene in human non-small cell lung cancer (Towbin H, Staehelin T, and Gordon P E. Electrophoretic transfer of proteins from polyacrylamide gels to nitrocellulose sheets: Procedure and some applications. Proc. Natl. Acad. Sci. USA 1979; 76:4350-4354; Allred D C, Harvey J M, Berardo M, et al: Prognostic and predictive factors in breast cancer by immunohistochemical analysis. Mod Pathol 1998; 11:155-168).

Additional powerful evidence of PKC-ι's importance in cellular malignancy includes its exclusive association with transformed phenotype of human melanomas in vivo and in vitro, it's overexpression in human non-small lung cancer cell lines, cholangiocarcinoma, and its presence in the transformed growth of human lung adenocarcinoma A549 cell line in vitro and tumorigenicity in vivo (Towbin H, Staehelin T, and Gordon P E. Electrophoretic transfer of proteins form polyacrylamide gels to nitrocellulose sheets: Procedure and some applications. Proc. Natl. Acad. Sci. USA 1979; 76:4350-4354; Allred D C, Harvey J M, Berardo M, et al: Prognostic and predictive factors in breast cancer by immunohistochemical analysis. Mod Pathol 1998; 11:155-168; Diaz-Meco, M. T., Municio, M. M., Sanchez, P., Lozano, J. and Moscat, J. Lamda-interacting protein, a novel protein that specifically interacts with the Zinc finger domain of the atypical Protein Kinase C isotype lambda/iota and stimulates its kinase activity in vitro and in vivo. Molec. and Cell Bio., 1996; 16: 105-114; Eder, A. M, Sui, X., Rosen, D. G., Nolden. L. K., Chen, K. W., Lahad, J. P., Kango-Singh, M., Lu, K. H., Warneke, C. L., Atkinson, E. N., Bedrosian, I., Keyomarsi, K., Kuo, W-l., Gray, J. W., Yin, J. C. P., Lui, J., Halder, G., Mills, G. B. Atypical PKC iota contributes to poor prognosis through loss of apical-basal polarity and Cyclin E overexpression in ovarian cancer. PNAS 2005; 102:12519-12524).

PKC-ι has been shown to be exclusively associated with the transformed phenotype of gliomas, benign and malignant meningiomas (Regala, R. P., Weems, C., Jamison, L., Copland, J. A. Thompson, E. A., Fields, A. P. Atypical protein kinase C iota plays a critical role in human lung cancer cell growth and tumorigenicity. J. Biol. Chem. 2005; 280:31109-31115). Elevated levels of PKC-ι have been correlated with poorer prognosis. Lung cancer patients who had elevated levels of PKC-ι during the early stages are 10 times more likely to die from the disease than those who had low levels of PKC-ι. PKC-ι has also been found to be involved in many oncogenic signaling pathways. PKC-α and PKC-δ are involved in the apoptosis of androgen dependent prostate cancer cells [16]. UV light induced overexpression of PKC-ε cause human squamous cell carcinoma [17]. PKC-ι is involved in androgen dependent prostate carcinoma and glioblastoma [18, 19]. PKC-β, PKC-γ, PKC-δ and PKC-ζ are also found to be involved in chronic lymphocytic leukemia [20].

Inhibitors of aPKC include, but are not limited to, 2-acetyl-1,3-cyclopentanedione (ACPD), 3,4, diamino-2,7-naphthalene disulfonic acid (DNDA), [4-(5-amino-4-carbamoylimidazol-1-yl)-2,3-dihydroxycyclopentyl] methyl dihydrogen phosphate (ICA-1), and 8-hydroxy-1, 3,6-naphthalenetrisulfonic acid (ζ-Stat).

ACPD is an inhibitor of atypical PKCs PKC-ι and PKC zeta (PKC-ζ). PKC-iota is a phosphorylating protein that plays a role in mediating apoptosis. PKC-zeta has been shown to contribute to survival of some cancer cells.

ICA-1 is an inhibitor of PKC-ι. DNDA, similar to ACPD, is a pan atypical PKC inhibitor, inhibiting PKC-ζ by about 80% and PKC-ι by about 20%.

ζ-Stat is an Inhibitor of PKC-ζ.

A linkage of the PKC family of proteins to colon cancer remains unknown. Given the implications of atypical PKCs in tumor formation and growth in general and the need for more efficient treatment of human colon cancer in particular, the instant invention provides methods for treating colon cancer by administering inhibitors of aPKCs.

BRIEF SUMMARY OF THE INVENTION

Provided herein are novel methods of treating colorectal cancers using atypical PKC (aPKC) inhibitors. In preferred embodiments, the instant invention relates to methods of treating colorectal cancer by administering to a subject in need thereof, a composition comprising a therapeutically effective amount of an inhibitor of an aPKC, including, but not limited to, PKC-ζ and PKC-ι. An inhibitor of an aPKC useful in the methods of the invention can inhibit PKC-ζ and/or PKC-ι. Non-limiting examples of inhibitors of PKC-ζ and/or PKC-ι useful in the methods of the instant invention include, but are not limited to, ACPD, DNDA, ICA-1, and ζ-Stat.

In further embodiments, the instant invention provides methods of measuring the susceptibility of colon cancer cells of a subject suffering from colon cancer to an aPKC inhibitor.

BRIEF DESCRIPTION OF THE DRAWINGS

For a fuller understanding of the invention, reference should be made to the following detailed description, taken in connection with the accompanying drawings, in which.

Blue diamond, control; orange square, 1.0 µM ζ-Stat; gray triangle, 1.5 µM ζ-Stat; yellow X, 2.0 µM ζ-Stat; and green circle, 3.0 µM ζ-Stat.

Figure 19:
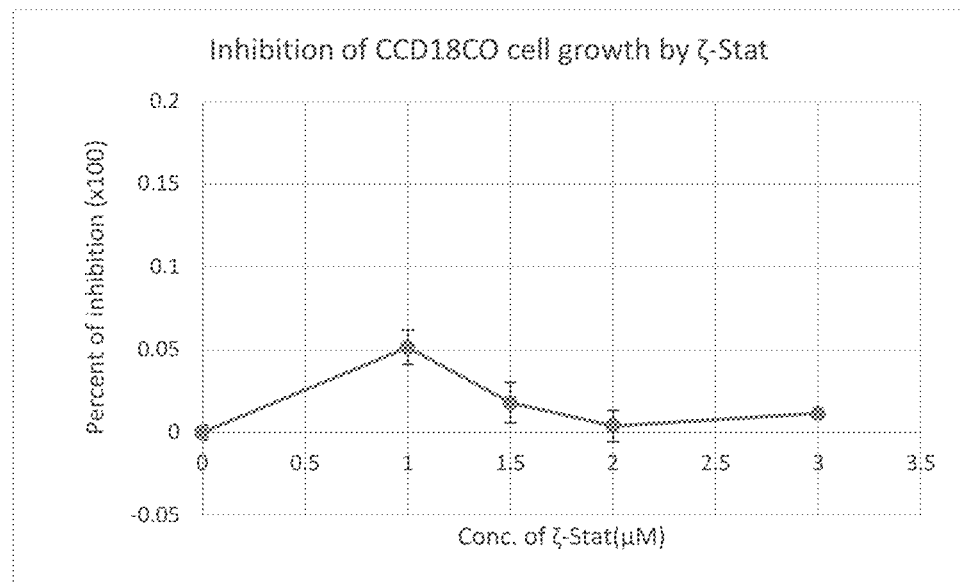

FIG. 19 shows the percentage of inhibition of CCD18CO cell growth by ζ-Stat.

Figure 20:
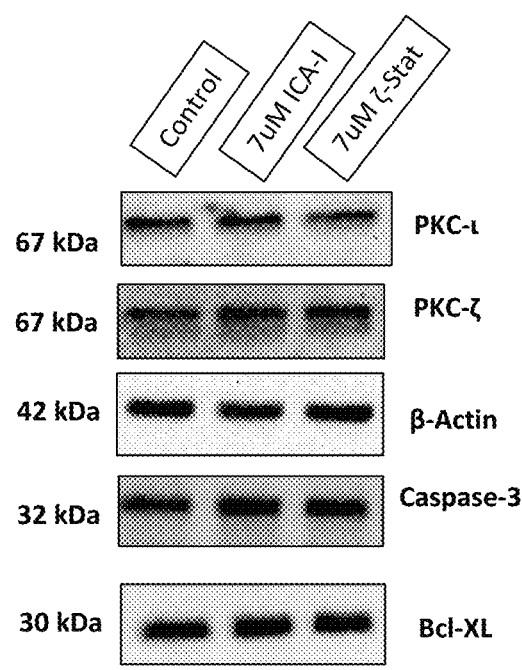

FIG. 20 shows the effects of specific aPKC inhibition by ICA-1 and ζ-Stat on CCD18CO normal colorectal cell survival.

DETAILED DISCLOSURE OF THE INVENTION

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supersedes any disclosure of an incorporated publication to the extent there is a contradiction.

Provided herein are methods of treating colorectal cancers using atypical PKC (aPKC) inhibitors. Further provided are methods of assessing the effectiveness of aPKC inhibitors in the effectiveness of inhibiting aPKCs in colon cancer cells of a subject suffering from colon cancer and the treatment of colon cancer in the subject in colon cancer cells obtained from a subject suffering from colon cancer.

In preferred embodiments, the instant invention provides methods of treating colorectal cancer by administering to a subject in need thereof, a composition comprising a therapeutically effective amount of an inhibitor of an aPKC.

The term "therapeutically effective amount," as used herein, refers to an amount that is capable of treating or ameliorating a disease or condition or otherwise capable of producing an intended therapeutic effect. In preferred embodiments, a therapeutically effective amount is an amount that is useful for treating a colon cancer disease.

The quantity to be administered, both according to number of treatments and unit dose, depends on the colon cancer disease and stage of colon cancer disease to be treated, the subject to be treated, the state of the subject and the susceptibility of the colon cancer disease to an inhibitor of an atypical PKC.

Precise amounts of the therapeutic composition also depend on the judgment of the practitioner and are peculiar to each individual. Generally, the dosage of the composition of the subject invention will vary depending upon such factors as the patient's age, weight, height, sex, general medical condition and previous medical history.

In some embodiments of the subject invention, the method comprises administration of multiple doses of the composition. The method may comprise administration of 1, 2, 3, 4, 5, 6, 7, 8, 9, 10, 15, 20, 25, 30, 35, 40, or more therapeutically effective doses of a composition comprising at least one of an atypical PKC as described herein. In some embodiments, doses are administered over the course of a short period of about 1 week to a long period of more than about 12 months. In some embodiment, the compositions according to the instant invention are administered for a period of about 2 weeks, 3 weeks, 4 weeks, 5 weeks, 6 weeks, 7 weeks, 10 weeks, 14 weeks, 20 weeks, 30 weeks, 40 weeks, 52 weeks or more than about 52 weeks.

For example, the compositions of the instant invention are administered from a low of about 1 week to a high of about 12 months; from about 2 weeks to about 50 weeks; from about 4 weeks to about 40 weeks; from about 6 weeks to about 30 weeks; from about 8 weeks to about 25 weeks; from about 10 weeks to about 20 weeks; from about 11 weeks to about 18 weeks; from about 12 weeks to about 17 weeks; or from about 14 to about 16 weeks.

The dosage of a composition according to the instant invention administered can be an amount from a low of about 0.1 µg/kg, about 0.5 µg/kg or about 1 µg/kg to a high of about 4000 mg/kg, about 4500 mg/kg or about 5000 mg/kg.

For example the amount of an inhibitor of an aPKC administered can be from about 0.1 µg/kg to about 5000 mg/kg; about 0.1 µg/kg to about 4500 mg/kg; about 0.1 µg/kg to about 4000 mg/kg; about 0.1 µg/kg to about 3000 mg/kg; about 0.1 µg/kg to about 2000 mg/kg; about 0.1 µg/kg to about 1500 mg/kg; about 0.1 µg/kg to about 1000 mg/kg; about 0.1 µg/kg to about 750 mg/kg; about 0.1 µg/kg to about 500 mg/kg; about 0.1 µg/kg to about 250 mg/kg; about 0.1 µg/kg to about 100 mg/kg; about 0.1 µg/kg to about 75 mg/kg; about 0.1 µg/kg to about 50 mg/kg; about 0.1 µg/kg to about 25 mg/kg; about 0.1 µg/kg to about 10 mg/kg; about 0.1 µg/kg to about 7.5 mg/kg; about 0.1 µg/kg to about 5 mg/kg; about 0.1 µg/kg to about 2.5 mg/kg; about 0.1 µg/kg to about 1 mg/kg; about 0.1 µg/kg to about 750 µg/kg; about 0.1 µg/kg to about 500 µg/kg; about 0.1 µg/kg to about 250 µg/kg; about 0.1 µg/kg to about 100 µg/kg; about 0.1 µg/kg to about 75 µg/kg; about 0.1 µg/kg to about 50 µg/kg; about 0.1 µg/kg to about 25 µg/kg; about 0.1 µg/kg to about 10 µg/kg; about 0.1 µg/kg to about 7.5 µg/kg; about 0.1 µg/kg to about 5 µg/kg; about 0.1 µg/kg to about 2.5 µg/kg; about 0.1 µg/kg to about 1 µg/kg; about 0.1 µg/kg to about 0.75 µg/kg; about 0.1 µg/kg to about 0.5 µg/kg; about 0.1 µg/kg to about 0.25 µg/kg.

The amount of an inhibitor of an aPKC administered can also be from about 0.2 µg/kg to about 5000 mg/kg; about 0.2 µg/kg to about 4500 mg/kg; about 0.2 µg/kg to about 4000 mg/kg; about 0.2 µg/kg to about 3000 mg/kg; about 0.2 µg/kg to about 2000 mg/kg; about 0.2 µg/kg to about 1500 mg/kg; about 0.2 µg/kg to about 1000 mg/kg; about 0.2 µg/kg to about 750 mg/kg; about 0.2 µg/kg to about 500 mg/kg; about 0.2 µg/kg to about 250 mg/kg; about 0.2 µg/kg to about 100 mg/kg; about 0.2 µg/kg to about 75 mg/kg; about 0.2 µg/kg to about 50 mg/kg; about 0.2 µg/kg to about 25 mg/kg; about 0.2 µg/kg to about 10 mg/kg; about 0.2 µg/kg to about 7.5 mg/kg; about 0.2 µg/kg to about 5 mg/kg; about 0.2 µg/kg to about 2.5 mg/kg; about 0.2 µg/kg to about 1 mg/kg; about 0.2 µg/kg to about 750 µg/kg; about 0.2 µg/kg to about 500 µg/kg; about 0.2 µg/kg to about 250 µg/kg; about 0.2 µg/kg to about 100 µg/kg; about 0.2 µg/kg to about 75 µg/kg; about 0.2 µg/kg to about 50 µg/kg; about 0.2 µg/kg to about 25 µg/kg; about 0.2 µg/kg to about 10 µg/kg; about 0.2 µg/kg to about 7.5 µg/kg; about 0.2 µg/kg to about 5 µg/kg; about 0.2 µg/kg to about 2.5 µg/kg; about 0.2 µg/kg to about 1 µg/kg; about 0.2 µg/kg to about 0.75 µg/kg; about 0.2 µg/kg to about 0.5 µg/kg; about 0.2 µg/kg to about 0.25 µg/kg.

The amount of an inhibitor of an aPKC administered can further be from about 0.5 µg/kg to about 5000 mg/kg; about 0.5 µg/kg to about 4500 mg/kg; about 0.5 µg/kg to about 4000 mg/kg; about 0.5 µg/kg to about 3000 mg/kg; about 0.5 µg/kg to about 2000 mg/kg; about 0.5 µg/kg to about 1500 mg/kg; about 0.5 µg/kg to about 1000 mg/kg; about 0.5 µg/kg to about 750 mg/kg; about 0.5 µg/kg to about 500 mg/kg; about 0.5 µg/kg to about 250 mg/kg; about 0.5 µg/kg to about 100 mg/kg; about 0.5 µg/kg to about 75 mg/kg; about 0.5 µg/kg to about 50 mg/kg; about 0.5 µg/kg to about 25 mg/kg; about 0.5 µg/kg to about 10 mg/kg; about 0.5 µg/kg to about 7.5 mg/kg; about 0.5 µg/kg to about 5 mg/kg; about 0.5 µg/kg to about 2.5 mg/kg; about 0.5 µg/kg to about 1 mg/kg; about 0.5 µg/kg to about 750 µg/kg; about 0.5 µg/kg to about 500 µg/kg; about 0.5 µg/kg to about 250 µg/kg; about 0.5 µg/kg to about 100 µg/kg; about 0.5 µg/kg to about 75 µg/kg; about 0.5 µg/kg to about 50 µg/kg; about 0.5 µg/kg to about 25 µg/kg; about 0.5 µg/kg to about 10 µg/kg; about 0.5 µg/kg to about 7.5 µg/kg; about 0.5 µg/kg to about 5 µg/kg; about 0.5 µg/kg to about 2.5 µg/kg; about 0.5 µg/kg to about 1 µg/kg; about 0.5 µg/kg to about 0.75 µg/kg.

The amount of an inhibitor of an aPKC administered can further be from about 1 µg/kg to about 5000 mg/kg; about 1 µg/kg to about 4500 mg/kg; about 1 µg/kg to about 4000 mg/kg; about 1 µg/kg to about 3000 mg/kg; about 1 µg/kg to about 2000 mg/kg; about 1 µg/kg to about 1500 mg/kg; about 1 µg/kg to about 1000 mg/kg; about 1 µg/kg to about 750 mg/kg; about 1 µg/kg to about 500 mg/kg; about 1 µg/kg to about 250 mg/kg; about 1 µg/kg to about 100 mg/kg; about 1 µg/kg to about 75 mg/kg; about 1 µg/kg to about 50 mg/kg; about 1 µg/kg to about 25 mg/kg; about 1 µg/kg to about 10 mg/kg; about 1 µg/kg to about 7.5 mg/kg; about 1 µg/kg to about 5 mg/kg; about 1 µg/kg to about 2.5 mg/kg; about 1 µg/kg to about 1 mg/kg; about 1 µg/kg to about 750 µg/kg; about 1 µg/kg to about 500 µg/kg; about 1 µg/kg to about 250 µg/kg; about 1 µg/kg to about 100 µg/kg; about 1 µg/kg to about 75 µg/kg; about 1 µg/kg to about 50 µg/kg; about 1 µg/kg to about 25 µg/kg; about 1 µg/kg to about 10 µg/kg; about 1 µg/kg to about 7.5 µg/kg; about 1 µg/kg to about 5 µg/kg; about 1 µg/kg to about 2.5 µg/kg.

The amount of an inhibitor of an aPKC administered can further be from about 2/kg to about 5000 mg/kg; about 2 µg/kg to about 4500 mg/kg; about 2 µg/kg to about 4000 mg/kg; about 2 µg/kg to about 3000 mg/kg; about 2 µg/kg to about 2000 mg/kg; about 2 µg/kg to about 1500 mg/kg; about 2 µg/kg to about 1000 mg/kg; about 2 µg/kg to about 750 mg/kg; about 2 µg/kg to about 500 mg/kg; about 2 µg/kg to about 250 mg/kg; about 2 µg/kg to about 100 mg/kg; about 2 µg/kg to about 75 mg/kg; about 21 µg/kg to about 50 mg/kg; about 2 µg/kg to about 25 mg/kg; about 2 µg/kg to about 10 mg/kg; about 2 µg/kg to about 7.5 mg/kg; about 2 µg/kg to about 5 mg/kg; about 2 µg/kg to about 2.5 mg/kg; about 2 µg/kg to about 1 mg/kg; about 21 µg/kg to about 750 µg/kg; about 2 µg/kg to about 500 µg/kg; about 2 µg/kg to about 250 µg/kg; about 2 µg/kg to about 100 µg/kg; about 2 µg/kg to about 75 µg/kg; about 2 µg/kg to about 50 µg/kg; about 2 µg/kg to about 25 µg/kg; about 2 µg/kg to about 10 µg/kg; about 2 µg/kg to about 7.5 µg/kg; about 2 µg/kg to about 5 µg/kg; about 2 µg/kg to about 2.5 µg/kg The amount of an inhibitor of an aPKC administered can further be from about 5 µg/kg to about 5000 mg/kg; about 5 µg/kg to about 4500 mg/kg; about 5 µg/kg to about 4000 mg/kg; about 5 µg/kg to about 3000 mg/kg; about 5 µg/kg to about 2000 mg/kg; about 5 µg/kg to about 1500 mg/kg; about 5 µg/kg to about 1000 mg/kg; about 5 µg/kg to about 750 mg/kg; about 5 µg/kg to about 500 mg/kg; about 5 µg/kg to about 250 mg/kg; about 5 µg/kg to about 100 mg/kg; about 5 µg/kg to about 75 mg/kg; about 5 µg/kg to about 50 mg/kg; about 5 µg/kg to about 25 mg/kg; about 5 µg/kg to about 10 mg/kg; about 5 µg/kg to about 7.5 mg/kg; about 5 µg/kg to about 5 mg/kg; about 5 µg/kg to about 2.5 mg/kg; about 5 µg/kg to about 1 mg/kg; about 5 µg/kg to about 750 µg/kg; about 5 µg/kg to about 500 µg/kg; about 5 µg/kg to about 250 µg/kg; about 5 µg/kg to about 100 µg/kg; about 5 µg/kg to about 75 µg/kg; about 5 µg/kg to about 50 µg/kg; about 5 µg/kg to about 25 µg/kg; about 5 µg/kg to about 10 µg/kg; about 5 µg/kg to about 7.5 µg/kg.

The amount of an inhibitor of an aPKC administered can further be from about 10 µg/kg to about 5000 mg/kg; about 10 µg/kg to about 4500 mg/kg; about 10 µg/kg to about 4000 mg/kg; about 10 µg/kg to about 3000 mg/kg; about 10 µg/kg to about 2000 mg/kg; about 10 µg/kg to about 1500 mg/kg; about 10 µg/kg to about 1000 mg/kg; about 10 µg/kg to about 750 mg/kg; about 10 µg/kg to about 500 mg/kg; about 10 µg/kg to about 250 mg/kg; about 10 µg/kg to about 100 mg/kg; about 10 µg/kg to about 75 mg/kg; about 10 µg/kg to about 50 mg/kg; about 10 µg/kg to about 25 mg/kg; about 10 µg/kg to about 10 mg/kg; about 10 µg/kg to about 7.5 mg/kg; about 10 µg/kg to about 5 mg/kg; about 10 µg/kg to about 2.5 mg/kg; about 10 µg/kg to about 1 mg/kg; about 10 µg/kg to about 750 µg/kg; about 10 µg/kg to about 500 µg/kg; about 10 µg/kg to about 250 µg/kg; about 10 µg/kg to about 100 µg/kg; about 10 µg/kg to about 75 µg/kg; about 10 µg/kg to about 50 µg/kg; about 10 µg/kg to about 25 µg/kg.

The amount of an inhibitor of an aPKC administered can further be from about 20 µg/kg to about 5000 mg/kg; about 20 µg/kg to about 4500 mg/kg; about 20 µg/kg to about 4000 mg/kg; about 20 µg/kg to about 3000 mg/kg; about 20 µg/kg to about 2000 mg/kg; about 20 µg/kg to about 1500 mg/kg; about 20 µg/kg to about 1000 mg/kg; about 20 µg/kg to about 750 mg/kg; about 20 µg/kg to about 500 mg/kg; about 20 µg/kg to about 250 mg/kg; about 20 µg/kg to about 100 mg/kg; about 20 µg/kg to about 75 mg/kg; about 20 µg/kg to about 50 mg/kg; about 20 µg/kg to about 25 mg/kg; about 20 µg/kg to about 10 mg/kg; about 20 µg/kg to about 7.5 mg/kg; about 20 µg/kg to about 5 mg/kg; about 20 µg/kg to about 2.5 mg/kg; about 20 µg/kg to about 1 mg/kg; about 20 µg/kg to about 750 µg/kg; about 20 µg/kg to about 500 µg/kg; about 20 µg/kg to about 250 µg/kg; about 20 µg/kg to about 100 µg/kg; about 20 µg/kg to about 75 µg/kg; about 20 µg/kg to about 50 µg/kg; about 20 µg/kg to about 25 µg/kg.

The amount of an inhibitor of an aPKC administered can further be from about 50 µg/kg to about 5000 mg/kg; about 50 µg/kg to about 4500 mg/kg; about 50 µg/kg to about 4000 mg/kg; about 50 µg/kg to about 3000 mg/kg; about 50 µg/kg to about 2000 mg/kg; about 50 µg/kg to about 1500 mg/kg; about 50 µg/kg to about 1000 mg/kg; about 50 µg/kg to about 750 mg/kg; about 50 µg/kg to about 500 mg/kg; about 50 µg/kg to about 250 mg/kg; about 50 µg/kg to about 100 mg/kg; about 50 µg/kg to about 75 mg/kg; about 50 µg/kg to about 50 mg/kg; about 50 µg/kg to about 25 mg/kg; about 50 µg/kg to about 10 mg/kg; about 50 µg/kg to about 7.5 mg/kg; about 50 µg/kg to about 5 mg/kg; about 50 µg/kg to about 2.5 mg/kg; about 50 µg/kg to about 1 mg/kg; about 50 µg/kg to about 750 µg/kg; about 50 µg/kg to about 500 µg/kg; about 50 µg/kg to about 250 µg/kg; about 50 µg/kg to about 100 µg/kg; about 50 µg/kg to about 75 µg/kg.

The amount of an inhibitor of an aPKC administered can further be from about 100 µg/kg to about 5000 mg/kg; about 100 µg/kg to about 4500 mg/kg; about 100 µg/kg to about 4000 mg/kg; about 100 µg/kg to about 3000 mg/kg; about 100 µg/kg to about 2000 mg/kg; about 100 µg/kg to about 1500 mg/kg; about 100 µg/kg to about 1000 mg/kg; about 100 µg/kg to about 750 mg/kg; about 100 µg/kg to about 500 mg/kg; about 100 µg/kg to about 250 mg/kg; about 100 µg/kg to about 100 mg/kg; about 100 µg/kg to about 75 mg/kg; about 100 µg/kg to about 50 mg/kg; about 100 µg/kg to about 25 mg/kg; about 100 µg/kg to about 10 mg/kg; about 100 µg/kg to about 7.5 mg/kg; about 100 µg/kg to about 5 mg/kg; about 100 µg/kg to about 2.5 mg/kg; about 100 µg/kg to about 1 mg/kg; about 100 µg/kg to about 750 µg/kg; about 100 µg/kg to about 500 µg/kg; about 100 µg/kg to about 250 µg/kg.

The amount of an inhibitor of an aPKC administered can further be from about 20 µg/kg to about 5000 mg/kg; about 200 µg/kg to about 4500 mg/kg; about 200 µg/kg to about 4000 mg/kg; about 200 µg/kg to about 3000 mg/kg; about 200 µg/kg to about 2000 mg/kg; about 200 µg/kg to about 1500 mg/kg; about 200 µg/kg to about 1000 mg/kg; about 200 µg/kg to about 750 mg/kg; about 200 µg/kg to about 500 mg/kg; about 200 µg/kg to about 250 mg/kg; about 200 µg/kg to about 100 mg/kg; about 200 µg/kg to about 75 mg/kg; about 200 µg/kg to about 50 mg/kg; about 200 µg/kg to about 25 mg/kg; about 200 µg/kg to about 10 mg/kg; about 200 µg/kg to about 7.5 mg/kg; about 200 µg/kg to about 5 mg/kg; about 200 µg/kg to about 2.5 mg/kg; about 200 µg/kg to about 1 mg/kg; about 200 µg/kg to about 750 µg/kg; about 200 µg/kg to about 500 µg/kg; about 200 µg/kg to about 250 µg/kg.

The amount of an inhibitor of an aPKC administered can further be from about 500 µg/kg to about 5000 mg/kg; about 500 µg/kg to about 4500 mg/kg; about 500 µg/kg to about 4000 mg/kg; about 500 µg/kg to about 3000 mg/kg; about 500 µg/kg to about 2000 mg/kg; about 500 µg/kg to about 1500 mg/kg; about 500 µg/kg to about 1000 mg/kg; about 500 µg/kg to about 750 mg/kg; about 500 µg/kg to about 500 mg/kg; about 500 µg/kg to about 250 mg/kg; about 500 µg/kg to about 100 mg/kg; about 500 µg/kg to about 75 mg/kg; about 500 µg/kg to about 50 mg/kg; about 500 µg/kg to about 25 mg/kg; about 500 µg/kg to about 10 mg/kg; about 500 µg/kg to about 7.5 mg/kg; about 500 µg/kg to about 5 mg/kg; about 500 µg/kg to about 2.5 mg/kg; about 500 µg/kg to about 1 mg/kg; about 500 µg/kg to about 750 µg/kg.

The amount of an inhibitor of an aPKC administered can further be from about 1 mg/kg to about 5000 mg/kg; about 1 mg/kg to about 4500 mg/kg; about 1 mg/kg to about 4000 mg/kg; about 1 mg/kg to about 3000 mg/kg; about 1 mg/kg to about 2000 mg/kg; about 1 mg/kg to about 1500 mg/kg; about 1 mg/kg to about 1000 mg/kg; about 1 mg/kg to about 750 mg/kg; about 1 mg/kg to about 500 mg/kg; about 1 mg/kg to about 250 mg/kg; about 1 mg/kg to about 100 mg/kg; about 1 mg/kg to about 75 mg/kg; about 1 mg/kg to about 50 mg/kg; about 1 mg/kg to about 25 mg/kg; about 1 mg/kg to about 10 mg/kg; about 1 mg/kg to about 7.5 mg/kg; about 1 mg/kg to about 5 mg/kg; about 1 mg/kg to about 2.5 mg/kg.

Advantageously, the administration of up to 5000 mg/kg of a composition comprising a aPKC inhibitor according to the instant invention in vivo in mice does not cause any toxicity.

The composition of the instant invention can be administered at once or several times per day. It is within the knowledge of the skilled clinician to determine the frequency and duration of administration of compositions of the instant invention.

In some embodiments, the PKC inhibitor is specific to a single aPKC. In certain embodiments, the aPKC inhibitor specific for a single aPKC is specific for PKC-ι. In preferred embodiments, the specific inhibitor of PKC-ι is ICA-1.

In other embodiments, the PKC inhibitor is a pan-aPKC inhibitor. In some embodiments, the pan-aPKC inhibitor is ACPD. In other embodiments, the pan-aPKC inhibitor is DNDA.

In certain preferred embodiments, the inhibitor is specific to PKC-ζ. In further preferred embodiments, the aPKC inhibitor specific for PKC-ζ is ζ-Stat.

In some embodiments, the methods of the instant invention provide treatment of a subject suffering from a colon cancer by administering a composition according to the invention, wherein the subject is a subject that suffers from colon cancer and the subject has cancer cells that are responsive to an inhibitor of an atypical PKC.

The colon cancers treated by methods of the instant invention include, but are not limited to, adenocarcinomas and squamous cell carcinomas.

The adenocarcinomas treated by the instant methods include, but are not limited to, carcinoid tumors, gastrointestinal stromal tumors including soft tissue sarcomas and sarcomas of blood vessels and connective tissue, and lymphomas of the colon.

The squamous cell carcinomas treated by the instant methods include, but are not limited to, carcinomas developing from blood vessels or smooth muscle cells of the colon, including leiomyosarcomas and angiosarcomas.

Further included in the instant methods of treating colon cancer are methods of treating colon cancer metastases, e.g. cancer cells that originate in the colon and spread to other organs in the subject's body. Also included are metastases to the colon, e.g. from cancers in other part of the intestine, e.g. the rectum, or other organs, which cells metastasize into the colon.

Further included in the instant methods of treating colon cancer are methods treating right colon cancer and left colon cancer.

The instant invention also provides methods of determining the susceptibility of the colon cancer cells of a subject to inhibitors of an aPKC.

In certain embodiments, the method of measuring the susceptibility of colon cancer cells of a subject suffering from colon cancer to an aPKC inhibitor, the method comprising:

obtaining a colon cell sample from a subject suffering from colon cancer, wherein the colon cell sample comprises cells suspected of being colon cancer cells and adjacent normal colon epithelial cells;

measuring the expression of an atypical PKC in the cells of the colon cell sample that are suspected of being colon cancer cells;

measuring the expression of an atypical PKC in the cells of the colon cell sample that are normal colon epithelial cells;

in the case of a higher expression of at least one atypical PKC in the cells of the colon cancer sample compared to the normal colon epithelial cells, exposing a portion of the colon cancer cells of the colon cell sample to an inhibitor of an aPKC according to the methods of the instant invention, while leaving another prion of the colon cancer cells of the colon cell sample untreated;

measuring cell proliferation, expression and activation of aPKCs and markers of apoptosis and anti-apoptosis in treated and untreated cells;

assigning the colon cancer cells of the subject as susceptible to methods of treatment by administering aPKC inhibitors according to the methods of the instant invention; and treating the subject according to the methods of the instant invention.

In certain embodiments, the methods of measuring the susceptibility of colon cancer cells of a subject suffering from colon cancer to an aPKC inhibitor include assigning the colon cancer cells of the subject as susceptible to an inhibitor of a aPKC when a decrease in the expression of an aPKC upon treatment of the cells with an inhibitor of a PKC is determined.

In certain embodiments, the methods of measuring the susceptibility of colon cancer cells of a subject suffering from colon cancer to an aPKC inhibitor include assigning the colon cancer cells of the subject as susceptible to an inhibitor of a aPKC when a decrease in the expression of an aPKC upon treatment of the cells with an inhibitor of a PKC is determined.

The phrase "susceptible to an aPKC inhibitor" indicates that upon administration of the colon cancer therapy comprising an aPKC inhibitor according to the instant invention, the subject exhibits beneficial or desired results including but not limited to therapeutic benefit; eradication, amelioration, delay or prevention of one or more of the symptoms of colon cancer; prolonging the life-span of the subject; or improvement in the quality of life of the subject. An improvement may be observed in the patient, notwithstanding that the patient may still be afflicted with colon cancer.

The phrase "non-susceptible to an aPKC inhibitor" according to the instant invention indicates that upon administration of the colon cancer therapy, the subject does not exhibit beneficial or desired results such as, therapeutic benefit; eradication, amelioration, delay or prevention of one or more of the symptoms of colon cancer; prolonging the life-span of the subject; or improvement in the quality of life of the subject.

It was advantageously determined that a subject having a colon cancer wherein the colon cancer cells from the subject exhibit a higher level and/or activity of mRNA or protein for PKC-ζ and/or PKC-ι is responsive to a colon cancer therapy with an inhibitor of PKC-ζ and/or PKC-ι.

The methods of measuring susceptibility of colon cancer cells to treatment with an inhibitor of an aPKC as provided herein are based on the measurement of a decreased expression of an aPKC in the colon cancer cells upon exposure to an aPKC inhibitor.

The methods of measuring susceptibility of colon cancer cells to treatment with an inhibitor of an aPKC as provided herein are further based on the measurement of a decreased phoshorylation of an aPKC in the colon cancer cells upon exposure to an aPKC inhibitor.

The methods of measuring susceptibility of colon cancer cells to treatment with an inhibitor of an aPKC as provided herein are also based on the measurement of a decreased expression of a caspase protein, including, but not limited to, caspase 3 in the colon cancer cells upon exposure to an aPKC inhibitor.

The methods of measuring susceptibility of colon cancer cells to treatment with an inhibitor of an aPKC as provided herein are further based on the measurement of a decreased expression of a survivin protein in the colon cancer cells upon exposure to an aPKC inhibitor.

The methods of measuring susceptibility of colon cancer cells to treatment with an inhibitor of an aPKC as provided herein are yet further based on the measurement of a decreased expression of a BCL protein, including, but not limited to, BCL-XL in the colon cancer cells upon exposure to an aPKC inhibitor.

Accordingly, in preferred embodiments of the subject invention, methods are provided for identifying a subject as responsive or non-responsive to a colon cancer therapy with an inhibitor of PKC-ζ and/or PKC-ι based on higher level and/or activity of mRNA or protein for PKC-ζ and/or PKC-ι in the colon cancer cells from the subject compared to control normal colon epithelial cell o the subject or normal colon epithelial cells of a control subject that is free of colon cancer cells.

In a certain embodiment, the subject invention provides a method of identifying a subject suffering from a colon cancer as responsive or non-responsive to a therapy with an inhibitor of PKC-ζ and/or PKC-ι. The method comprises the steps of:

(a) determining the level and/or activity of PKC-ζ and/or PKC-ι mRNA or protein in a test sample obtained from the subject, (b) optionally, determining the level and/or activity of PKC-ζ and/or PKC-ι mRNA or protein in a control sample, or obtaining a reference value corresponding to the level of PKC-ζ and/or PKC-ι mRNA or protein; and (i) identifying the subject as being responsive to the colon cancer therapy with the inhibitor of PKC-ζ and/or PKC-ι based on the level and/or activity of PKC-ζ and/or PKC-ι mRNA or protein in the test sample as compared to the level and/or activity of PKC-ζ and/or PKC-ι mRNA or protein in the control sample, and optionally, administering the colon cancer therapy with the inhibitor of PKC-ζ and/or PKC-ι to the subject identified as being responsive; or (ii) identifying the subject as being non-responsive to the colon cancer therapy with the inhibitor of PKC-ζ and/or PKC-ι based the level and/or activity of PKC-ζ and/or PKC-ι mRNA or protein in the test sample as compared to the level and/or activity of PKC-ζ and/or PKC-ι mRNA or protein in the control sample, and optionally, administering a colon cancer therapy other than the colon cancer therapy with the inhibitor of PKC-ζ and/or PKC-ι to the subject identified as being non-responsive.

In specific embodiments, the test samples comprise the colon cancer cells from the subject.

It was advantageously determined that a subject's colon cancer cells are responsive to a colon cancer therapy with an inhibitor of PKC-ζ and/or PKC-ι if the colon cancer cells in the subject contain a higher level and/or activity of mRNA or protein for PKC-ζ and/or PKC-ι in the colon cancer cells compared to non-cancer normal colon epithelial cells.

It was also determined that a subject's colon cancer is non-responsive to a colon cancer therapy with an inhibitor of PKC-ζ and/or PKC-ι if the colon cancer cells in the subject contain a similar or lower level and/or activity of mRNA or protein for PKC-ζ and/or PKC-ι in the colon cancer cells from the subject compared to the control normal colon epithelial cells of the subject.

Various techniques are known to a person of ordinary skill in the art to determine the level of mRNA in a sample. Non-limiting examples of such techniques include microarray analysis, real-time polymerase chain reaction (PCR), Northern blot, in situ hybridization, solution hybridization, or quantitative reverse transcription PCR (qRT-PCR). Methods of carrying out these techniques are routine in the art. Additional methods of determining the level of mRNA in a sample are also well known to a person of ordinary skill in the art and such embodiments are within the purview of the invention.

Various techniques are known to a person of ordinary skill in the art to determine the level of PKC-ζ and/or PKC-ι protein in a sample. Non-limiting examples of such techniques include protein array analysis, Western blot analysis, enzyme-linked immunosorbent assay (ELISA), radio-immune assay (RIA), etc. Methods of carrying out these techniques are routine in the art. Additional methods of determining the level of PKC-ζ and/or PKC-ι protein in a sample are also known to a person of ordinary skill in the art and such embodiments are within the purview of the invention.

Similarly, various techniques are known to a person of ordinary skill in the art to determine the activity of PKC-ζ and/or PKC-ι protein in a sample. Methods of carrying out activity assays of PKC-ζ and/or PKC-ι protein are known in the art and are within the purview of the invention.

A reference value corresponding to the level of mRNA or protein for PKC-ζ and/or PKC-ι indicates the level of mRNA or protein for PKC-ζ and/or PKC-ι in the colon cancer cells of a subject that is responsive or non-responsive to a colon cancer therapy with an inhibitor of PKC-ζ and/or PKC-ι. As such, a reference value corresponding to the level of mRNA or protein for PKC-ζ and/or PKC-ι may be indicative of the subject being responsive or non-responsive to a colon cancer therapy with an inhibitor of PKC-ζ and/or PKC-ι.

To practice the methods of the subject invention described herein for identifying a subject as being responsive or non-responsive to a melanoma therapy with an inhibitor of PKC-ζ and/or PKC-ι, a control sample can be one or more of the following:

a) normal colon epithelial cells from an individual belonging to the same species as the subject and not having colon cancer, b) normal colon epithelial cells from the subject prior to getting melanoma, c) normal colon epithelial cells from the subject not affected by colon cancer, d) colon cancer cells from an individual known to be responsive to a colon cancer therapy with an inhibitor of PKC-ζ and/or PKC-ι, or e) colon cancer cells from an individual known to be non-responsive to a colon cancer therapy with an inhibitor of PKC-ζ and/or PKC-ι.

Additional examples of control samples that can be used in the invention can be designed by a person of ordinary skill in the art and such embodiments are within the purview of the invention.

In certain embodiments, the subject used in the invention is a mammal. Non-limiting examples of mammals include human, ape, canine, pig, bovine, rodent, or feline.

Once a subject is identified as being responsive to a colon cancer treatment with an inhibitor of PKC-ζ and/or PKC-ι based on the methods of the subject invention, the steps of treating and/or managing colon cancer include administering to the subject one or more inhibitors of PKC-ζ and/or PKC-ι described herein.

In preferred embodiments, a colon cancer treatment with an inhibitor of PKC-ζ and/or PKC-ι is administered to the subject in combination with one or more additional colon cancer therapies. Such additional melanoma therapies can be therapies that do not inhibit PKC-ζ and/or PKC-ι, a surgery, a radiation therapy, an immunotherapy or a combination thereof.

In other preferred embodiments, two inhibitors of inhibitor of PKC-ζ and/or PKC-ι are administered to the subject in combination.

In further preferred embodiments, the two inhibitors of PKC-ζ and/or PKC-ι that are administered to the subject in combination are administered in a way that each inhibitor is administered at a sub-therapeutic level.

Once a subject is identified as being non-responsive to a colon cancer treatment with an inhibitor of PKC-ζ and/or PKC-ι based on the methods described herein, the step of treating and/or managing colon cancer includes administering to the subject one or more colon cancer therapies other than an inhibitor of PKC-ζ and/or PKC-ι. Examples of colon cancer therapies other than an inhibitor of PKC-ζ and/or PKC-ι include a surgery, a radiation therapy, an immunotherapy or a combination thereof.

In specific preferred embodiments, the subject invention provides a novel atypical PKC inhibitor that is specific to PKC-ζ. In further preferred embodiments, the novel atypical PKC inhibitor specific to PKC-ζ is 8-hydroxy-1, 3,6-naphthalenetrisulfonic acid (ζ-Stat). Advantageously, the novel PKC-ζ specific inhibitor can decrease the levels of total and phosphorylated PKC-ζ without affecting PKC-ι. In preferred embodiments of the subject invention, the PKC-ζ specific inhibitor ζ-Stat inhibits cellular signaling pathways that are involved in endothelial-to-mesenchymal transition (EMT) of colon cancer cells. Further advantageously, the PKC-ζ specific inhibitor ζ-Stat effectively suppresses PKC-ζ mediated EMT and induces apoptosis in colon cancer cells.

In further embodiments, methods of inhibiting colon cancer proliferation are provided. In preferred embodiments, the methods comprise contacting the colon cancer cells with a therapeutically effective amount of an inhibitor of an aPKC, for example, PKC-ι and PKC-ζ.

In some embodiments, the PKC inhibitor administered to inhibit colon cancer proliferation is specific to a single aPKC, for example, PKC-ι. In a preferred embodiment, the specific inhibitor of PKC-ι is ICA-1.

In other embodiments, the PKC inhibitor administered to inhibit colon cancer proliferation is a pan-aPKC inhibitor. In preferred embodiments, the pan-aPKC inhibitor is ACPD. In some embodiments, the pan-aPKC inhibitor is DNDA.

In preferred embodiments, the PKC inhibitor administered to inhibit colon cancer proliferation is specific to a single aPKC, for example, PKC-ιt. In some preferred embodiments, the specific aPKC inhibitor is ICA-1.

In further preferred embodiments, the PKC inhibitor administered to inhibit colon cancer proliferation is specific to PKC-ζ. In certain preferred embodiments, the specific inhibitor of PKC-ζ is ζ-Stat.

An inhibitor of an aPKC useful in the methods of the invention can inhibit PKC-ζ and/or PKC-ι. Non-limiting examples of inhibitors of PKC-ζ and/or PKC-ι useful in the methods of the instant invention include, but are not limited to, ACPD, DNDA, ICA-1, and ζ-Stat.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. In some embodiments, the term "about" represents up to ±15%.

The composition of the subject invention can comprise a pharmaceutically acceptable carrier and/or excipient comprising substances, such as an inert vehicle, or pharmaceutical acceptable adjuvants, and can contain preservatives and additives usual for injection solutions, such as stabilizing agents, salts or saline, and/or buffers etc. Examples pharmaceutically acceptable substances are well known to a person of ordinary skill in the art and such embodiments are within the purview of the current invention.

The pharmaceutical composition may be a liquid formulation or a solid formulation. When the pharmaceutical composition is a solid formulation it may be formulated as a tablet, a sucking tablet, a chewing tablet, a chewing gum, a capsule, a sachet, a powder, a granule, a coated particle, a coated tablet, an enterocoated tablet, an enterocoated capsule, a melting strip or a film. When the pharmaceutical composition is a liquid formulation it may be formulated as an oral solution, a suspension, an emulsion or syrup. Said composition may further comprise a carrier material independently selected from, but not limited to, the group consisting of lactic acid fermented foods, fermented dairy products, resistant starch, dietary fibers, carbohydrates, proteins, and glycosylated proteins.

Pharmaceutical compositions, as disclosed herein, can be formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. Pharmaceutical composition according to the invention may also be formulated to release active agents substantially immediately upon administration or at any predetermined time or time period after administration.

Exemplary modes of administration include oral, rectal, transmucosal, topical, transcervical, transuterine, transurethral, transdermal, inhalation, parenteral (e.g., intravenous, subcutaneous, intradermal, intramuscular, and intraarticular) administration. Injectables can be prepared in conventional forms, either as liquid solutions or suspensions, solid forms suitable for solution or suspension in liquid prior to injection, or as emulsions. Alternatively, one may administer the composition of the subject invention in a local rather than systemic manner, for example, in a depot or sustained-release formulation.

Materials And Methods

Cell Lines and Subculture:

The colon cancerous cell line, HT-29 and normal colon epithelial cells, CCD18CO were obtained from American Type Tissue Culture Collection. The HT-29 cells and CCD18CO cells were subculture and maintained in T75 flasks containing McCoy's media and Eagle's Minimum Essential Media respectively, both of the flasks were supplemented with 10% FBS (Fetal Bovine Serum) and 1% antibiotics (Penicillin 10 U/ml and streptomycin 10 mg/ml). Cells were incubated at 37° C. and 5% $CO_2$. After few days of incubation following subculture, cells were used at 70-80% confluency for the experiment.

Antibodies and Reagents:

ζ-Stat or Compound 50 or 8-hydroxy-1, 3, 6-naphthalenetrisulfonic acid was purchased from National Cancer Institute (NCI). It was dissolved in sterile water before use. PKC-ι antibody was purchased from BD Biosciences (San Jose, Calif.). The antibodies to Phospho PKC-ζ (T410), phosphor AKT (S473), Caspase-3, Cleaved Caspase-3 and BCL-XL were purchased from Cell signaling Technology (Danvers, Mass.). The antibodies purchased from Thermo Fisher Scientific were PKC-ζ, β-actin and survivin. phospho PKC-ι (T555) was purchased from Invitrogen Inc. Enhanced Chemiluminescence (Super Signal West Pico Chemiluminescent Substrate) was Purchased from Pierce (Rockford, Ill.). McCOY'S 5A medium was purchased from GE Healthcare Life Sciences (South Logan, Utah), Eagle's minimum essential medium was procured from Corning (Manassas, Va.) and Trypsin-EDTA (ethylene diamine tetra-acetic acid) solution was obtained from Fisher Scientific (Norcross, Ga.).

In-Vitro Treatment of HT-29 Colon Cancer Cell with DNDA, ACPD, ICA-1, and ζ-Stat:

Cells ($3.0 \times 10^4$/well) were grown as monolayer on 6 wells plate. After incubation for 24 hrs, the cells were treated with 0.25 μM, 0.50 μM, 0.75 μM, 1.0 μM, 1.5 μM, 2 μM, and 3 μM of ACPD, ICA-1, DNDA or ζ-Stat for three consecutive days. Cells are then washed (2 ml 2× DPBS buffer), trypsinized, resuspended in McCoy's 5A media and counted with hemocytometer, Scepter & MTT assay.

Scratch Wound Healing Assay:

Cells were plated into 6-well plates, at approximately 90% confluent and a line scratched across the cell monolayer using a 100-μL pipette tip. Cells were treated using 0.5 μM, 1.5 μM and 3.0 μM of DNDA, ACPD and ICA-1. The cells that moved to the interspace of the wound line were counted at 24 hrs, 48 hrs and 72 hrs intervals using a phase contrast microscope (Motic, China). This assay was repeated 3 times.

Immunoblot Analysis:

Cells were cultured ($9.0 \times 10^4$) in 100 mm cell culture flasks. After incubation for 24 hours (to get least 50% confluency), fresh media was supplied and each experimental flasks were treated with 0.5 μM, 0.75 μM, 1.0 μM, 1.5 μM, 2.0 μM, 3.0 μM, 5.0 μM and 7.0 μM with ζ-Stat, ACPD, and DNDA. Equal volume of sterile water (vehicle control) as the volume of drug was added in the control also. Treatment was continued for three consecutive days. Total cell-lysates were prepared and subjected to western blot analysis for aPKC analysis.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1: Effect of Atypical PKC Inhibitors on Colon Cancer

Figure 1:
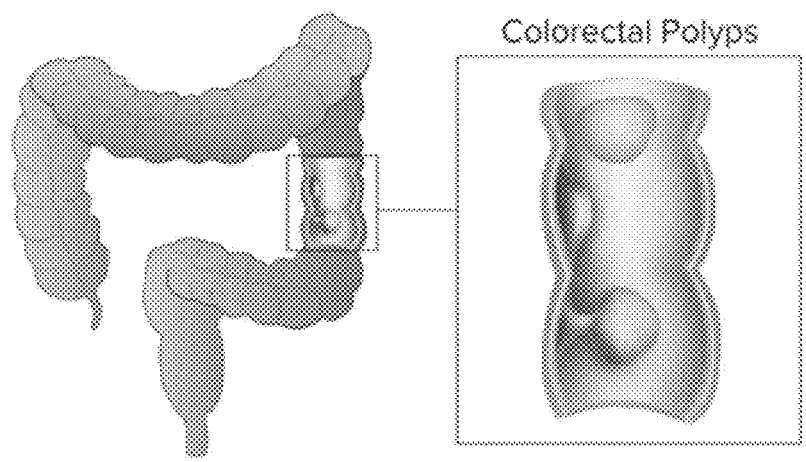
FIG. 1 shows an image of the development of colorectal polyps that can lead to cancer over time.
Figure 2:
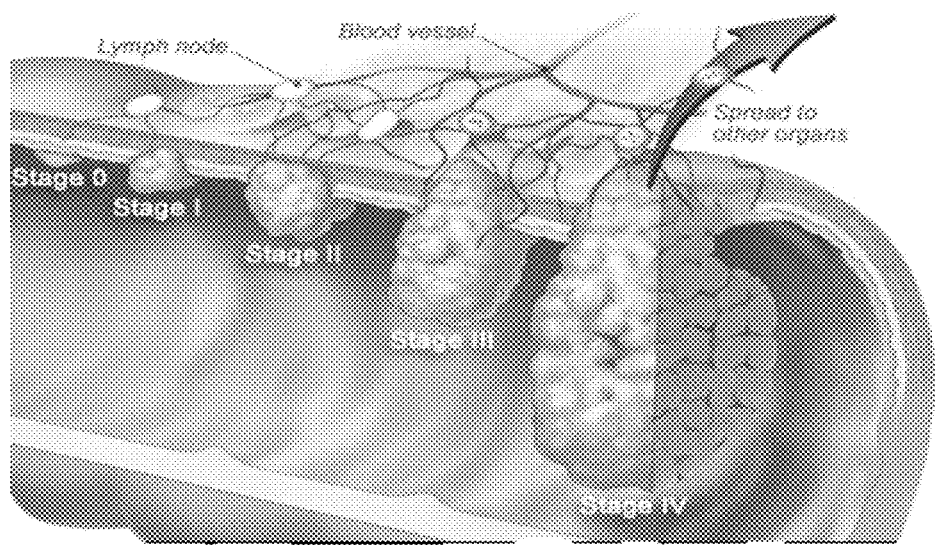
FIG. 2 shows an image of the stages of colorectal cancer.

FIG. 1 shows an image of the development of colorectal polyps which can lead to cancer over time. FIG. 2 shows an image of the different stages of colorectal cancer. Colorectal cancer (CRC) is the development of cancer in the colon or rectum due to the abnormal growth of cells that have the ability to invade or spread to other parts of the body [4]. Colorectal cancer often begins as a growth called a polyp, which may form on the inner wall of the colon or rectum (FIG. 1.1). Over time, polyps may become malignant [2]. Colorectal cancers are mostly adenocarcinomas.

Figure 3:
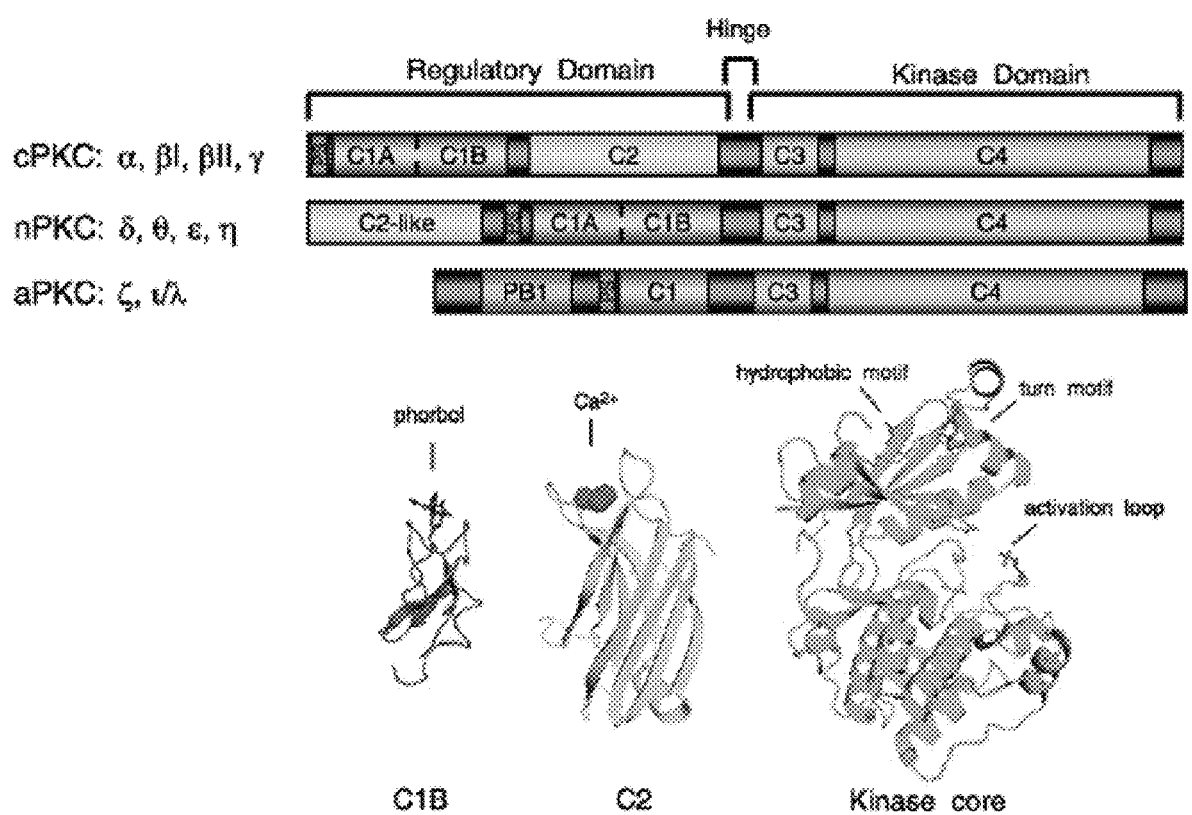
FIG. 3 shows a series of images of the domain structure of protein kinase C (PKC) isoforms.

A comparison of the domain structures of protein kinase C (PKC) isoforms including conventional PKCs (cPKCs), novel PKCs (nPKCs) and atypical PKCs (aPKCs) indicates the similarities between the kinase domains and the hydrophobic motif, the turn motif and the activation loop of the kinase core (FIG. 3). PKCs have a conserved kinase domain (depicted in teal) and more variable regulatory domains. All PKC regulatory domains have an auto-inhibitory pseudo-substrate motif (shown in green) and an $NH_2$ terminal to the C1 domain (shown in pink). Tandem C1 domains are the molecular sensors of phorbol 12-myristate 13-acetate (PMA)/diacylglycerol (DAG) in cPKC and nPKC isoforms, whereas the single aPKC C1 domain does not bind DAG/PMA. The C2 domains (in yellow) function as calcium-dependent phospholipid binding modules in cPKCs. nPKC C2 domains do not bind calcium; the PKCδ-C2-like domain is a phosphotyrosine interaction module. PKC isoform variable regions are shown in gray. Bottom: ribbon diagrams of PKC C1B domain, C2 domain, and kinase domain structures [14]. After being freed from PS-dependent auto-inhibition, some lipids play important roles. In case of conventional and novel PKCs some membrane lipids such as phosphatidylserine, and lipid metabolites like diacylglycerol (DAG) cause release of pseudosubstrate from the active sites and resulting in phosphorylation of PKC substrate proteins [38].

Figure 4:
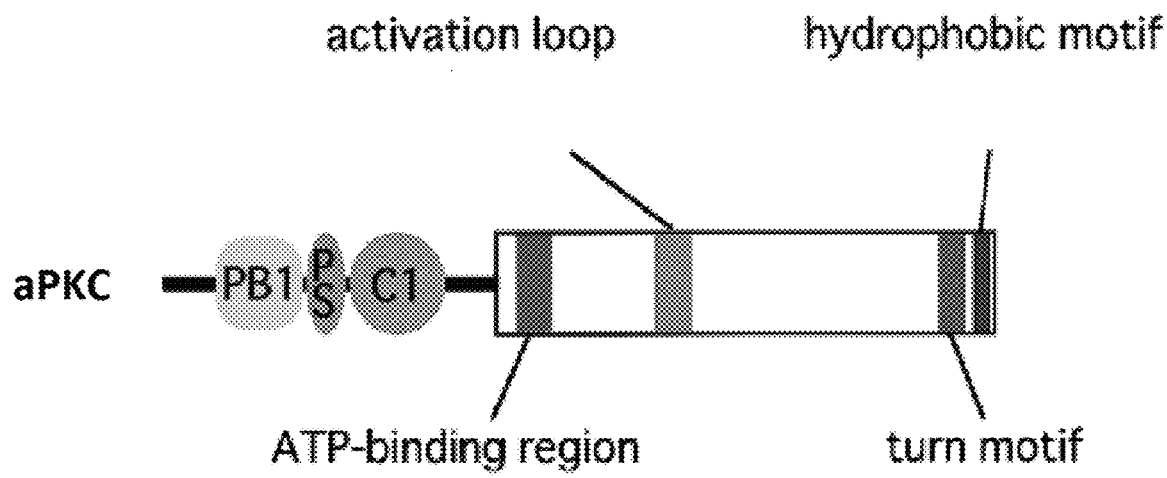
FIG. 4 shows a schematic representation of the domain structures of aPKC.

FIG. 4 shows a schematic representation of the domain structures of aPKC. The N-terminus of the aPKC has a PB1 domain required for protein-protein interaction with MEK5, PAR-6 and p62, a pseudosubstrate, a C1 domain and a Ser/Thr kinase (also called catalytic) domain in the C-terminus. The kinase domain has ATP binding site, activation loop, turn motif and hydrophobic motif. Thr-403 in PKC-ι and Thr-410 in PKC-ζ in the activation loop need to be phosphorylated (possibly by PDK-1 or Akt) in order to activate the enzymes [37].

Between atypical PKCs, PKC-ι is proven to be a potential oncogene in many cancers whereas the role of the highly homologous aPKC PKC-ζ has not explored in terms of carcinogenesis. In this study, a novel specific PKC-ζ inhibitor called ζ-Stat or Compound 50 or 8-hydroxy-1, 3, 6-naphthalenetrisulfonic acid is used to assess the role of this particular PKC enzyme in colon carcinogenesis. We found that the inhibition of PKC-ζ by ζ-Stat specifically reduces the risk of colon carcinogenesis. Therefore, it might be used as a potential chemotherapeutic agent for cancer treatment.

Example 2: The Effects of Atypical PKC Inhibitor ACPD on a Colon Cancer Cell Line HT-29

To determine the understanding behind the complex mechanisms involved the inventors investigated multiple inhibitors of aPKC: ACPD and DNDA are pan-aPKC inhibitors and ICA-1 as an inhibitor of PKC-ι in colon cancer cell lines. ACPD is an inhibitor of atypical PKC-ι and PKC-ζ. PKC-ι is a phosphorylating protein that plays a role in mediating apoptosis. PKC-ζ has been shown to contribute to survival of some cancer cells. Both ICA-1 and ACPD are inhibitors of PKC-ι and ACPD inhibits both PKC-ι and PKC-ζ. DNDA, similar to ACPD, is a pan aPKC inhibitor, inhibiting PKC-ζ by about 80% and PKC-ι by about 20%.

HT-29 cells were treated with five different concentrations of ACPD for 24-72 hours. After starting treatment, viable cells were counted at each 24 hours interval using Tryphan blue exclusion assay and scepter. The data represents n=4 independent experiments.

Figure 5:
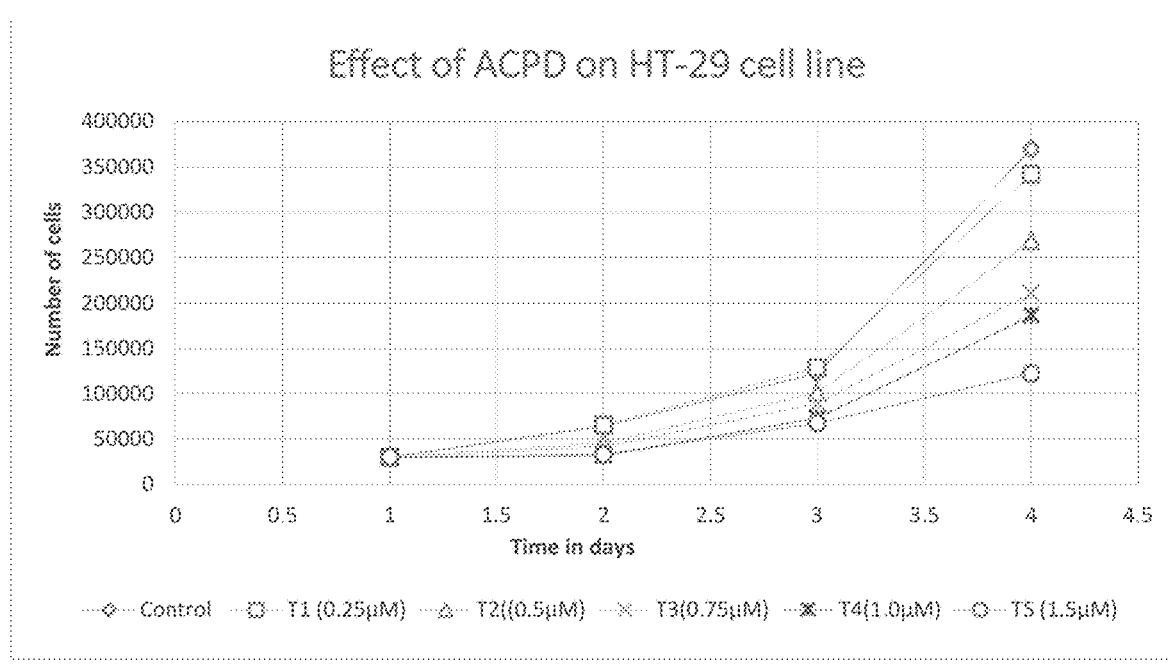
FIG. 5 shows the effect of ACPD on the HT-29 colon cancer cell line. The number of HT-29 cells decreases as the concentration of ACPD increases over time. Blue diamond, control; orange square, 0.25 μM ACPD; gray triangle, 0.5 μM ACPD; yellow X, 0.75 μM ACPD; blue X, 1.0 μM ACPD; and green circle, 1.5 μM ACPD.
Figure 6:
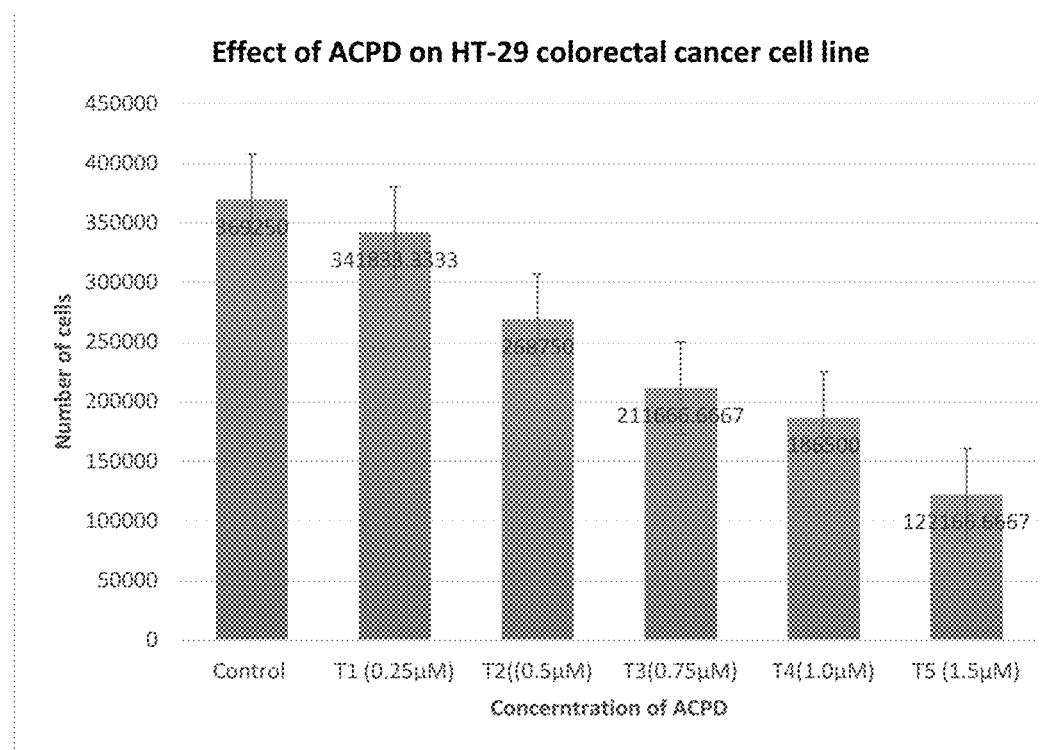
FIG. 6 shows the accumulated effect of ACPD treatment on the HT-29 colon cancer cells line after three days of treatment. At this time, HT-29 cells had a slight decrease in proliferation at 0.25 μM and a dramatic decrease in proliferation at 1.5 μM concentration of ACPD.
Figure 7:
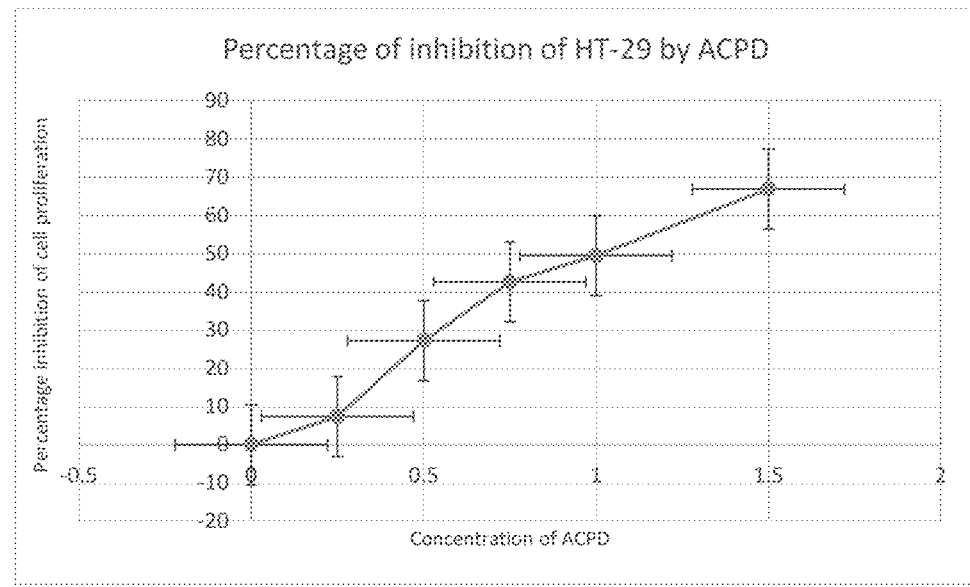
FIG. 7 shows the percentage of inhibition of HT-29 cell growth by ACPD. The percentage of inhibition of the HT-29 colon cancer cells by ACPD increases as a function of ACPD. The growth of the cells decreases by 50 percent (half, $IC_{50}$) at approximately 1.0 μM.

ACPD decreased cell proliferation in a dose-dependent manner over an exposure time of 4 days (FIG. 5). Within the first three days of treatment, the number of HT-29 cells decreased as the concentration of ACPD increased. As shown in FIG. 6, after three days post treatment, HT-29 cells had a slight decrease in proliferation at 0.25 µM and a dramatic decrease in proliferation at 1.5 µM concentration of ACPD. The percentage of inhibition of the HT-29 colon cancer cells by ACPD increased as a function of ACPD; a decrease of growth of HT-29 cells by 50 percent (half, $IC_{50}$) occurred at approximately 1.0 µM. (FIG. 7).

Example 3: The Effects of Atypical PKC Inhibitor DNDA on a Colon Cancer Cell Line HT-29

HT-29 cells were treated with five different concentrations of DNDA for 24-72 hours. After starting treatment, viable cells were counted at each 24 hours interval using Tryphan blue exclusion assay and scepter. The data represents n=4 independent experiments.

Figure 8:
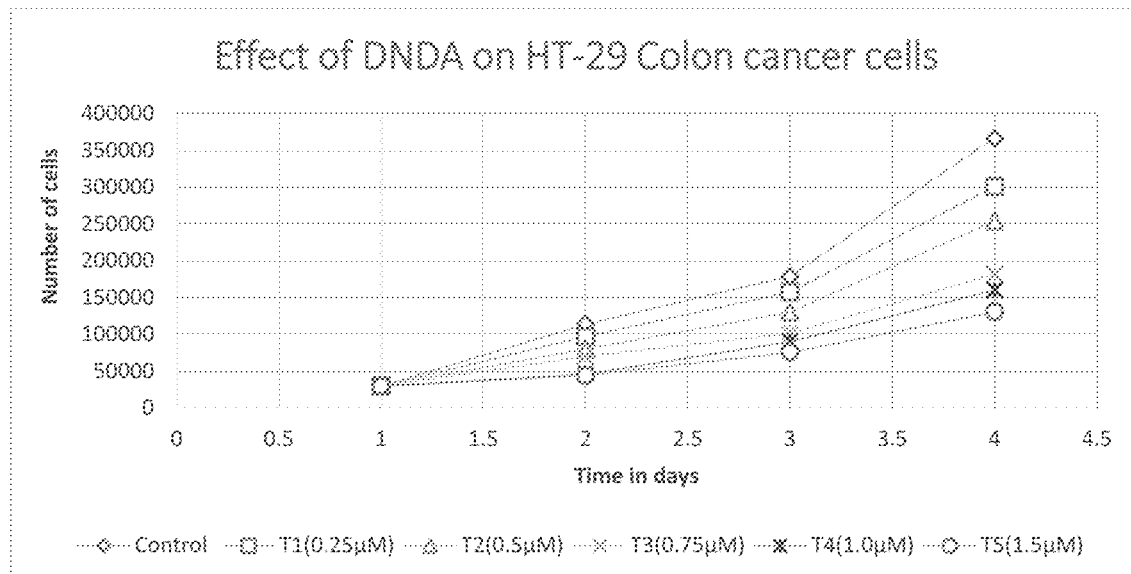
FIG. 8 shows the effect of DNDA on the HT-29 colon cancer cell line. The number of HT-29 cells decreases as the concentration of DNDA increases over time. Blue diamond, control; orange square, 0.25 μM DNDA; gray triangle, 0.5 μM DNDA; yellow X, 0.75 μM DNDA; blue X, 1.0 μM DNDA; and green circle, 1.5 μM DNDA.
Figure 9:
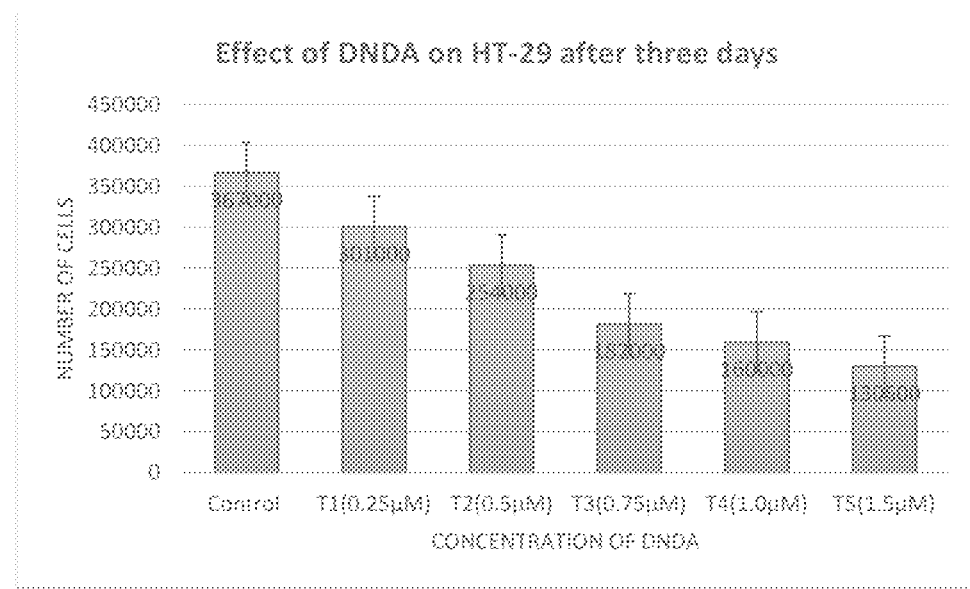
FIG. 9 shows the accumulated effect of DNDA treatment on the HT-29 colon cancer cell line after three days of treatment. At this time, HT-29 cells showed a slight decrease in proliferation at 0.25 μM of DNDA and a dramatic decrease in proliferation at 1.5 μM concentration of DNDA.
Figure 10:
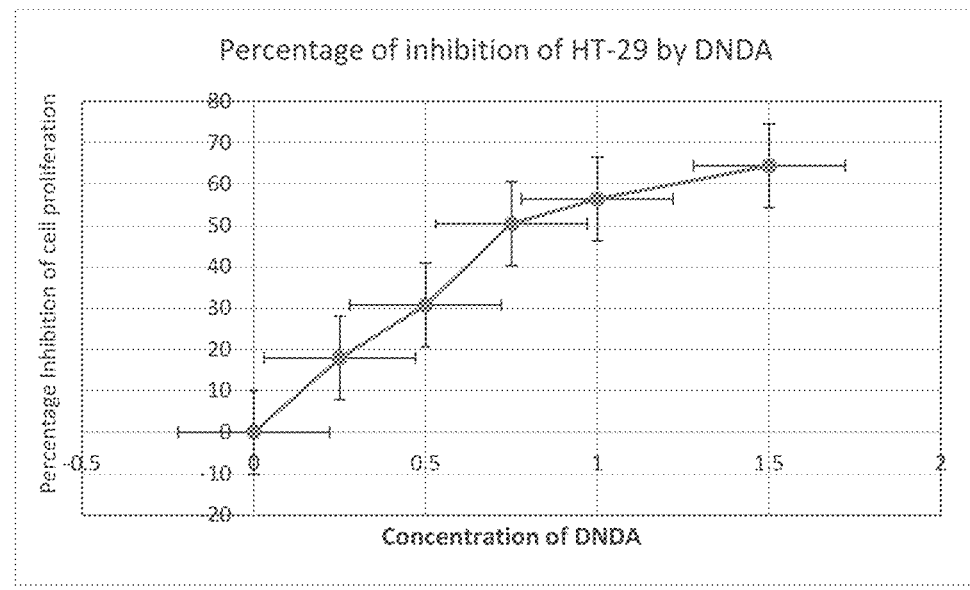
FIG. 10 shows the percentage of inhibition of HT-29 cell growth by DNDA. The percentage inhibition of the HT-29 colon cancer cells by DNDA increases as a function of DNDA. The growth of the cells decreases by 50 percent (half, $IC_{50}$) at approximately 0.78 μM.

DNDA acts in a similar manner to decrease colon cancer cell proliferation in a dose-dependent manner as illustrated in FIGS. 8-10. The number of HT-29 cells decreased as the concentration of DNDA increased over time (FIG. 8). After three days post treatment, HT-29 cells had a slight decrease in proliferation at 0.25 µM of DNDA and a dramatic decrease in proliferation at 1.5 µM concentration of DNDA (FIG. 9). The percentage of inhibition of the HT-29 colon cancer cells by DNDA increased as a function of DNDA; a decrease of growth of HT-29 cells by 50 percent (half, $IC_{50}$) occurred at approximately 0.78 µM (FIG. 10).

Example 4: The Effects of Atypical PKC Inhibitor ICA-1 on a Colon Cancer Cell Line HT-29

HT-29 cells were treated with five different concentrations of ICA-1 for 24-72 hours. After starting treatment, viable cells were counted at each 24 hours interval using Tryphan blue exclusion assay and scepter. The data represents n=4 independent experiments.

Figure 11:
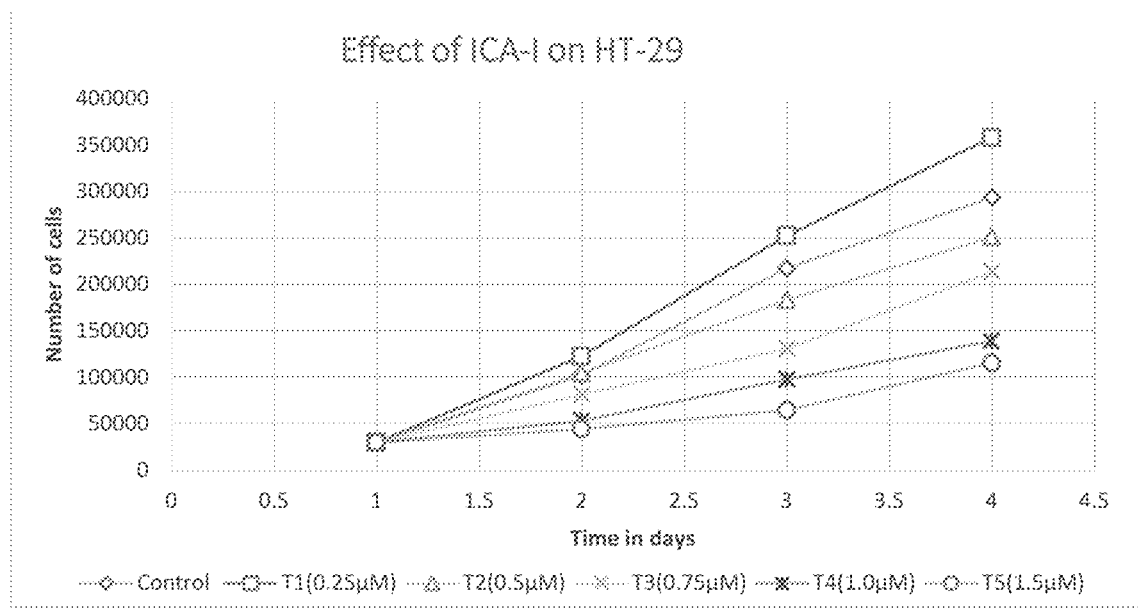
FIG. 11 shows the effect of ICA-1 on the HT-29 colon cancer cell line. The number of HT-29 cells decreases as the concentration of ICA-I increases over time. Blue diamond, control; orange square, 0.25 μM ICA-1; gray triangle, 0.5 μM ICA-1; yellow X, 0.75 μM ICA-1; blue X, 1.0 μM ICA-1; and green circle, 1.5 μM ICA-1.
Figure 12:
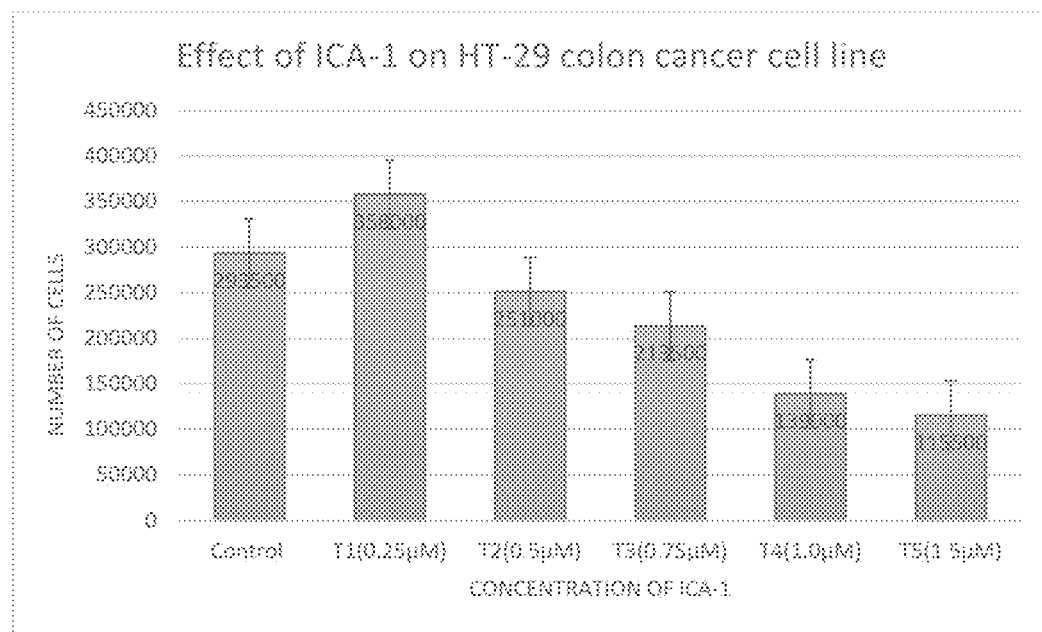
FIG. 12 shows the accumulated effect of ICA-1 treatment on the HT-29 colon cancer cell line after three days of treatment. At this time, ICA-1 had a slight increase in cell proliferation at 0.25 μM and a dramatic decrease in cell proliferation at 1.5 μM of ICA-1.
Figure 13:
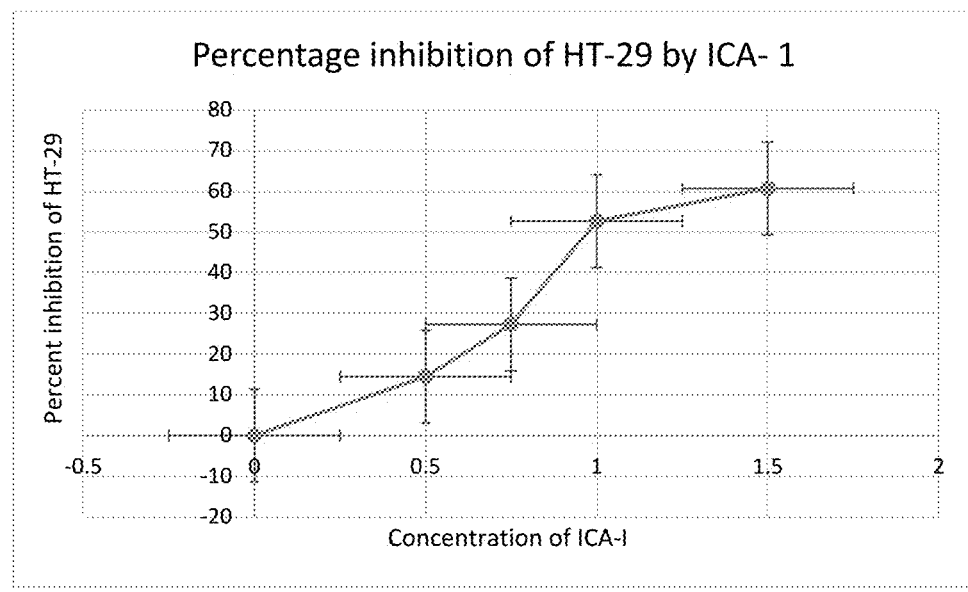
FIG. 13 shows the percentage of inhibition of HT-29 cell growth by ICA-1. The percentage of inhibition of the HT-29 colon cancer cells increases as a function of ICA-1. The growth of the cells reduces by 50 percent (half, $IC_{50}$) at approximately 0.95 μM.

ICA-1 also acts in a similar manner to decrease colon cancer cell proliferation in a dose-dependent manner as illustrated in FIGS. 11-13. The number of HT-29 cells decreased as the concentration of ICA-I increased over time (FIG. 11). After three days of post treatment, ICA-1 caused a slight increase in cell proliferation at 0.25 µM and a dramatic decrease in cell proliferation at 1.5 µM of ICA-1 (FIG. 12). The percentage of inhibition of the HT-29 colon cancer cells increased as a function of ICA-1; a decrease of growth of HT-29 cells by 50 percent (half, $IC_{50}$) occurred at approximately 0.95 µM (FIG. 13).

Both ACPD and ICA-1 showed a slight increase in cell proliferation at concentrations of 0.25 µM while at this same concentration DNDA showed a slight decrease. At low concentrations ACPD and ICA-1 may be inhibiting phosphorylation of a tumor suppressor and at higher concentrations ACPD and ICA-1 inhibit phosphorylation of other substrates. Given the results from the studies, each drug should be administered at a minimum concentration of at least the $IC_{50}$ of the respective drug. These results indicate the therapeutic potential of aPKC inhibitors for the treatment of colon cancer.

Example 5: The Effects of Atypical PKC Inhibitor ζ-Stat on a Colon Cancer Cell Line HT-29

Figure 14:
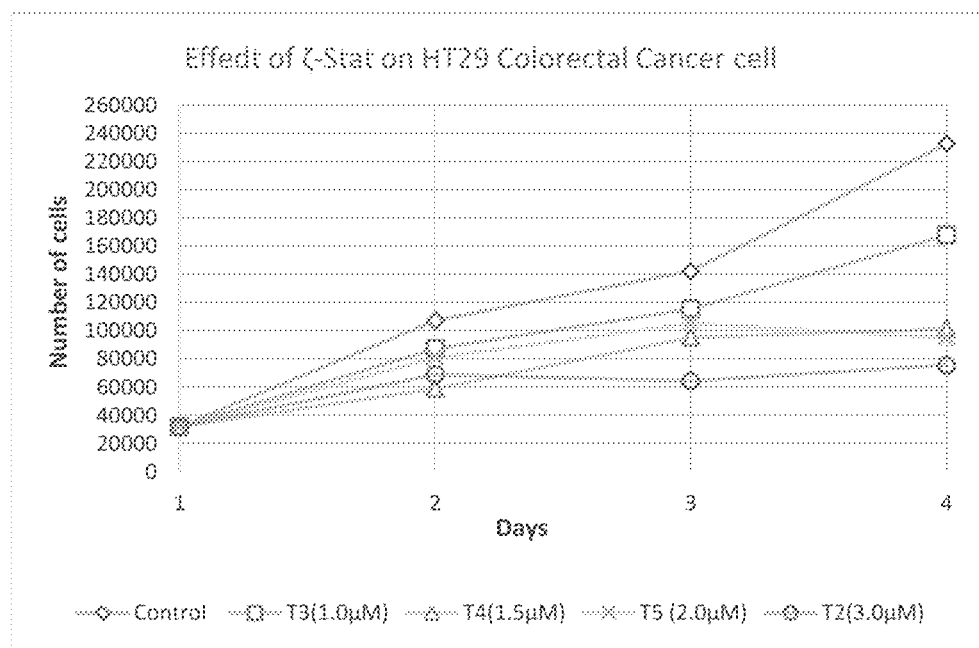
FIG. 14 shows the effect of ζ-Stat on HT-29 colorectal cancer cell line. The number of HT-29 cells decreases as the concentration of ζ-Stat increases over time. Blue diamond, control; orange square, 1.0 μM ζ-Stat; gray triangle, 1.5 μM ζ-Stat; yellow X, 2.0 μM ζ-Stat; and green circle, 3.0 μM ζ-Stat.
Figure 15:
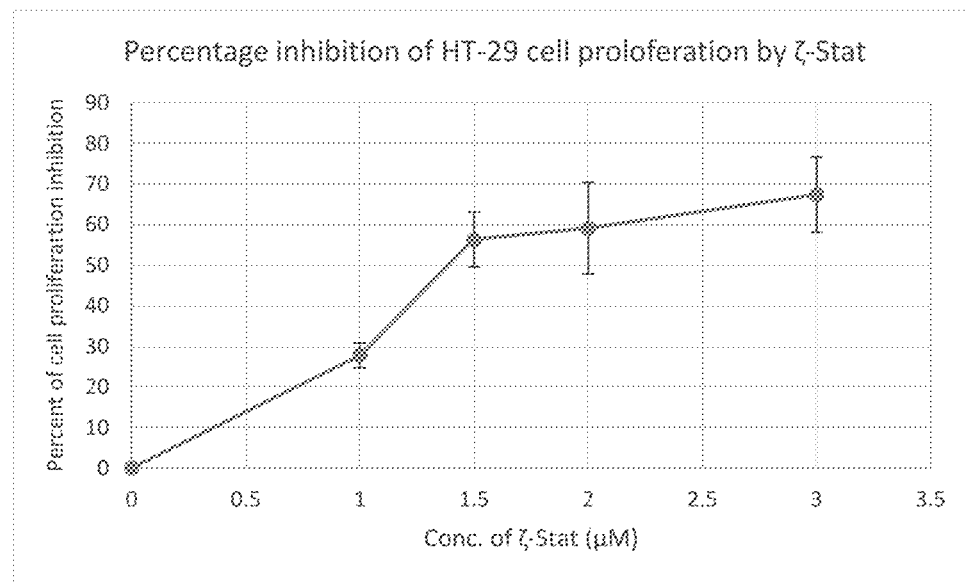
FIG. 15 shows percentage inhibition of HT-29 cell growth by ζ-Stat.

HT-29 cells were treated with four different concentrations of ζ-Stat for 24-72 hours. After starting treatment, viable cells were counted at each 24 hours interval using Tryphan blue exclusion assay and scepter. The data represents n=4 independent experiments.

ζ-Stat inhibits colon cancer cell proliferation in a dose-dependent manner. The number of HT-29 cells decreased as the concentration of ζ-Stat increased over time (FIG. 14). After three days of post treatment, ζ-Stat caused a dramatic decrease in cell proliferation at 1.5 µM of ζ-Stat (FIG. 15). The percentage of inhibition of the HT-29 colon cancer cells increased as a function of ζ-Stat; a decrease of growth of HT-29 cells by 50 percent (half, $IC_{50}$) occurred at approximately 1.4 µM (FIG. 15). The results demonstrate that the ζ-Stat is capable of inhibiting the HT-29 cells by about 60% upon treatment over three days (FIG. 15).

Example 6: The Effects of Atypical PKC Inhibitor ζ-Stat on aPKC Expression and Phosphorylation in a Colon Cancer Cell Line HT-29

Figure 16:
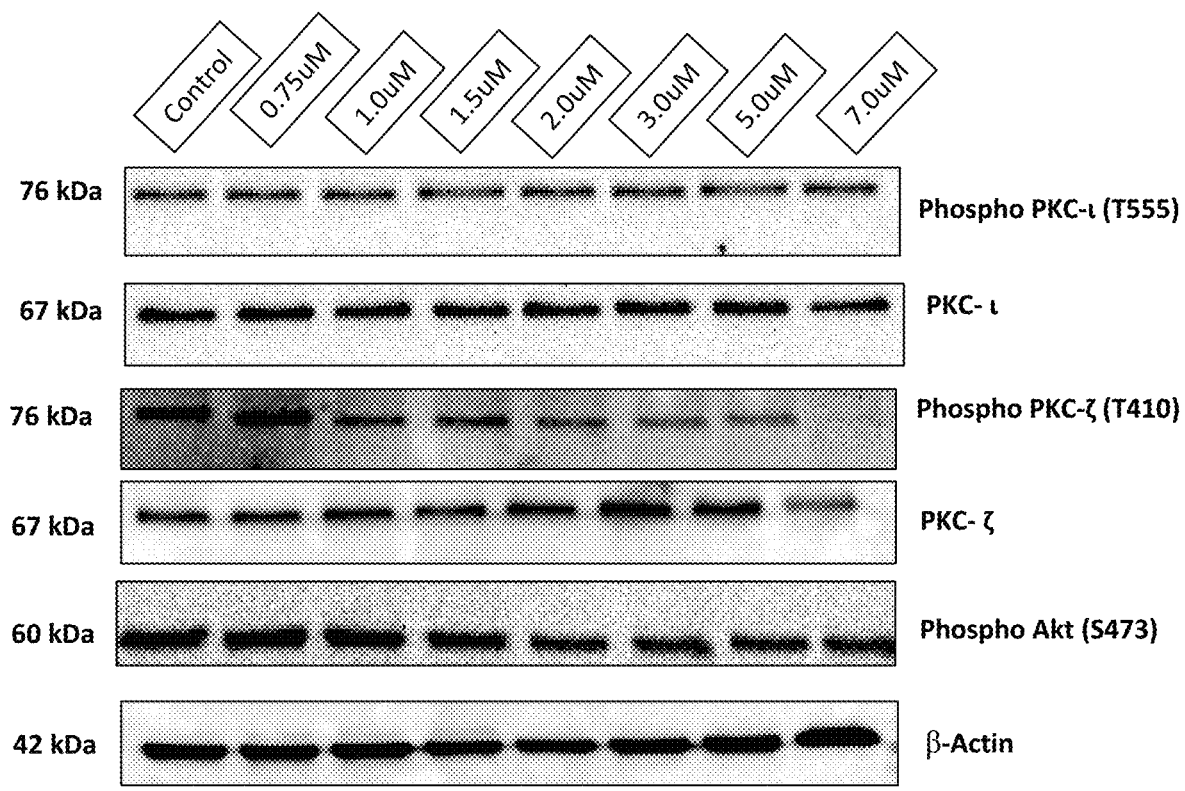
FIG. 16 shows the effect of ζ-Stat on the expression and phosphorylation of PKC-ι and PKC-ζ in the HT-29 colorectal cancer cell line.

Because PKC-ι and PKC-ζ are homologous (84%) in terms of amino acids sequence of their catalytic domain [7], the specificity of the effect of ζ-Stat on PKC-ζ was tested by performing western blot analysis. HT-29 colorectal cancerous cells were treated with seven different concentrations of ζ-Stat for 72 hours, harvested and whole cell extracts were prepared. Equal amounts (40 µg) of protein were loaded on SDS-PAGE followed by immunoblotting for pPKC-ι(T555), PKC-ι, pPKC-ζ(T410), PKC-ζ, pAKT(S473) and β-actin to examine the effect of ζ-Stat on those protein levels. Data represents n=3 independent observations. A selective decrease in the phosphorylation of PKC-ζ was observed upon increasing concentrations of ζ-Stat. The results suggest that the ζ-Stat specifically inhibits PKC-ζ not PKC-ι (FIG. 16).

Figure 17:
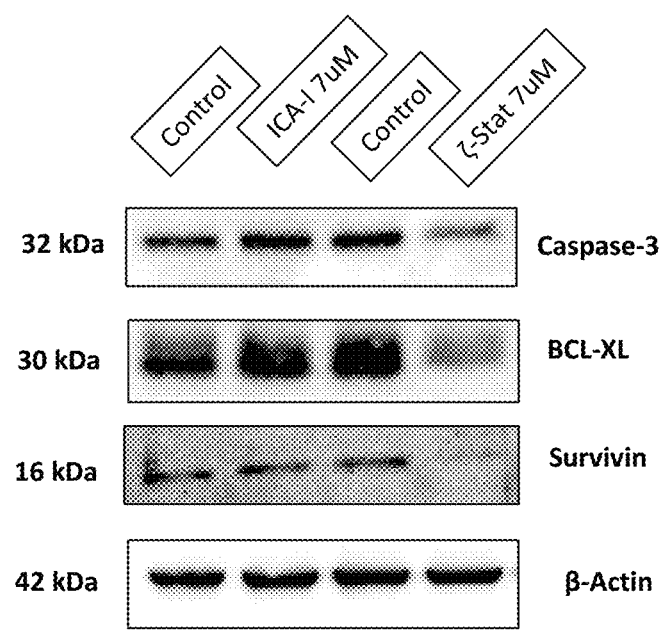
FIG. 17 shows the effect of specific aPKC inhibition on HT-29 colorectal cancer cell survival.

Example 7: The Effects of Atypical PKC Inhibitors ICA-1 and ζ-Stat on HT-29 Colorectal Cancer Cell Survival HT-29 colorectal cancer cells were treated with 7 µM ICA-I or 7 µM ζ-Stat for 72 hours, harvested and whole cell lysates were prepared. Equal amounts (40 µg) of protein were loaded on SDS-PAGE followed by immunoblotting for Caspase-3, BCL-XL, Survivin and β-actin to determine the effects of specific aPKC inhibition on survival and apoptotic proteins. Data represents n=3 independent experiments. The results suggest that ζ-Stat also decreases the level of pro-survival proteins (FIG. 17).

Figure 18:
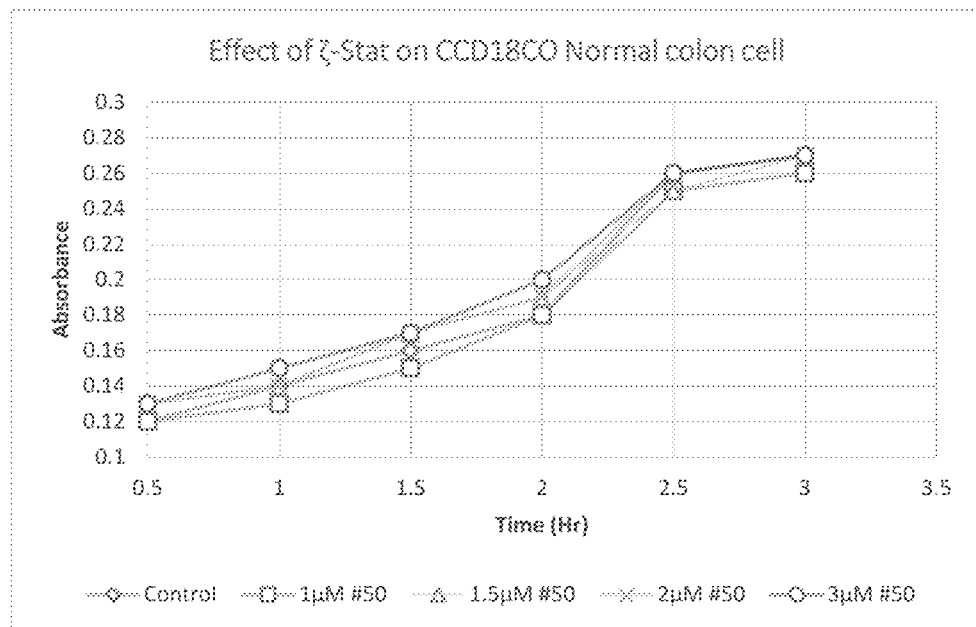
FIG. 18 shows the effect of ζ-Stat on the normal colon epithelial cell line CCD18CO. The number of HT-29 cells did not change with increasing concentrations of ζ-Stat.

Example 8: The Effects of Atypical PKC Inhibitor ζ-Stat on Normal Colon Epithelial Cell Proliferation To establish the efficacy of ζ-Stat as a specific inhibitor of PKC-ζ, the effect of ζ-Stat on CCD18CO normal colon epithelial cell line was tested. CCD18CO normal epithelial cell line cells were treated with four different concentrations of ζ-Stat for three consecutive days followed by incubation with MTT reagent and taking absorbance reading at each half an hour interval for three hours at 577 nm using microplate reader. The data represents n=3 independent experiments. The results indicate that ζ-Stat is not toxic to the normal epithelial (FIGS. 17 and 18).

Example 9: The Effects of Atypical PKC Inhibitor ζ-Stat on Normal Colon Epithelial Cell Growth The percentage of inhibition of CCD18C0 cell growth was measured after three hours of MTT incubation. The percent inhibition of cells growth was less than 10% which is statistically insignificant. The data represents n=3 independent replicates (FIG. 19).

Example 10: The Effects of Atypical PKC Inhibitor ζ-Stat on Normal Colon Epithelial Cell Survival CCD18CO cells were treated with 7 µM ICA-I or 7 µM ζ-Stat, respectively, for 72 hours, harvested and whole cell lysates were prepared. Equal amounts (40 µg) of protein were loaded on SDS-PAGE followed by immunoblotting for PKC-ι, PKC-ζ, Caspase-3, BCL-XL, and β-actin to see the effect of specific aPKC inhibition on survival and apoptotic proteins. Data represents n=3 independent experiments. The results indicate that ICA-1 and ζ-Stat are not toxic to normal epithelial cells even at concentrations of 7 µM (FIG. 20).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Jemal A, Bray F, Center M M, et al. Global cancer statistics. CA Cancer J Clin 2011; 61:69.
2. "Colorectal Cancer Overview" & "A snapshot of colorectal cancer". National Cancer Institute. Retrieved 1 Feb. 2016.
3. Calvert P M, Frucht H. The genetics of colorectal cancer. Ann Intern Med. 2002 October 1; 137 (7):603-12.
4. "Defining Cancer". National Cancer Institute. Retrieved 1 Feb. 2016.
5. G. Steven Martin. Cell signaling and Cancer. Cell Press Volume 4, Issue 3, September 2003, Pages 167-174.
6. Nishizuka Y, 1992. Intracellular signaling by hydrolysis of phospholipids and activation of protein kinase C. Science. 1992 Oct. 23; 258(5082):607-14.
7. Lisa A. Selbie, Carsten Schmitz-Peiffer, Yonghua Sheng, and Trevor J. Biden, 1993. Molecular Cloning and Characterization of PKC iota, an Atypical Isoform of Protein Kinase C Derived from Insulin-secreting Cell. The Journal of Biological Chemistry. Vol. 268, No. 32, Issue of November 15, pp. 24296-24302, 1993.
8. Nelson D l, Cox M M, Biosignaling. Lehninger Principles of Biochemistry. $3^{rd}$ edition. New York: Worth Publishers; 2001. P. 469.
9. William T. Couldwell, Jack P. Antel, Michael L. J. Apuzzo, and Voon Wee Yong. Inhibition of growth of established human glioma cell lines by modulators of the protein kinase-C system. Journal of Neurosurgery October 1990/Vol. 73/No. 4/Pages 594-600.
10. Kishimoto A., Takai Y., Mori T., Kikkawa U., Nishizuka Y. (1980). Activation of calcium and Phosholipid dependent protein kinase by diacylglycerol, its possible relation to phophotidylinositol turnover. Journal of Biological Chemistry. 255: 2273-2276.
11. Castagna M., Takai Y., Kaibuchi K., Kikkawa U., Nishizuka Y. (1982). Direct activation of calcium activated, phospholipid dependent protein kinase by tumor promoting phorbol ester. Journal of Biological Chemistry. 257: 7847-51.

12. Johannes, F. J., Eis, S, Oberhagemann P., Pfizermaier, K (1994). PKC mu is a novel atypical member of the protein kinase family. Journal of Biological Chemistry; 269: 61408.
13. Palmer, R. H., Ridden, J., (1995). Clonning and expression pattern of two members of a novel Protein kinase C related family. Eur J Biochem; 227: 344-351.
14. Alexandra C. Newton (1995). Protein Kinase C: Structure, Function, and Regulation. JBC Dec. 1, 1995 vol. 270 no. 48 28495-28498.
15. Goa, Toker A and Alexandra C. Newton (2001). The carboxy terminus of protein kinase C provides a switch to regulate its interaction with the phosphonositide-dependent kinase, PDK-1. Journal of biological chemistry; 276: 6461-6468.
16. Gavrielides M V, Frijhoff A F, Conti C J, Kazanietz M G (2005). Protein kinase C and prostate carcinogenesis: targeting the cell cycle and apoptotic mechanisms. 5:431-443.
17. Wheeler D L, LI Y, Verma A K (2005). Protein kinase Cε ultraviolet light induced cutaneous damage and development of squamous cell carcinoma possibly through induction of specific cytokines in a paracrine mechanism. Photochem Photibiol; 81: 9-18.
18. Andrae N. MCCray, Shraddha Desai, Mildred acevedo-Duncan (2013). The interruption of PKC-ι signaling and TRAIL combination therapy against glioblastoma cells. NeuroChem Res; 39: 1691-1701.
19. H. Y. Win and Mildred Acevedo-Duncan (2007). Role of Protein Kinase C-iota in transformed non-malignant RWPE-1 cells and androgen-independent prostate carcinoma DU-145 cells. Cell Prolif; 42: 182-194.
20. Alkan S, Huang Q Ergin M et. al. (2005) PKC in Chronic lymphocytic leukemia and determination of isoform expression pattern and genes altered by PKC inhibition. AM J Hematol; 79:97-106.
21. Nicole R Murray, Lee Jamieson, Wangsheng Yu, Jie Zhang, Yesim Gokmen-polar, Deborah Sier, Panos Anastasiadis, Zoran Gatalica, E. Aubrey Thompson, and Alan p. Fields (2004). Protein kinase Cι is required for Ras transformation and colon carcinogenesis in vivo. JCB; 164: 797-802.
22. Rodriguez S, Wang L, Mumaw C, Srour E F, Lo Celso C, Nakayama K, Carlesso N. The SKP2 E3 ligase regulates basal homeostasis and stress-induced regeneration of HSCs. *Blood* 2011; 117: 6509-6519 [PMID: 21502543 DOI: 10.1182/blood-2010-11-321521].
23. Wang Z, Gao D, Fukushima H, Inuzuka H, Liu P, Wan L, Sarkar F H, Wei W. Skp2: a novel potential therapeutic target for prostate cancer. *Biochim Biophys Acta* 2012; 1825: 11-17 [PMID: 21963805 DOI: 10.1016/j.bbcan.2011.09.002].
24. Chan C H, Lee S W, Wang J, Lin H K. Regulation of Skp2 expression and activity and its role in cancer progression. *Scientific World Journal* 2010; 10: 1001-1015 [PMID: 20526532 DOI: 10.1100/tsw.2010.89].
25. Kitagawa, M., Lee, S. H., and McCormick, F. (2008) Skp2 suppresses p53-dependent apoptosis by inhibiting p300. Mol. Cell 29, 217-231.
26. Wang, H., Bauzon, F., Ji, P., Xu, X., Sun, D., Locker, J., Sellers, R. S., Nakayama, K., Nakayama, K. I., Cobrinik, D., and Zhu, L. (2010) Skp2 is required for survival of aberrantly proliferating Rb1-deficient cells and for tumorigenesis in Rb1+/− mice. Nat. Genet. 42, 83-88.
27. Ji, P., Jiang, H., Rekhtman, K., Bloom, J., Ichetovkin, M., Pagano, M., and Zhu, L. (2004) An Rb-Skp2-p27 pathway mediates acute cell cycle inhibition by Rb and is retained in a partial-penetrance Rb mutant. Mol. Cell 16, 47-58. 47. Dehan, E. and Pagano, M. (2005) Skp2, the FoxO1 hunter. Cancer Cell 7, 209-210.
28. Chan, C. H., Lee, S. W., Li, C. F., Wang, J., Yang, W. L., Wu, C. Y., Wu, J., Nakayama, K. I., Kang, H. Y., Huang, H. Y., Hung, M. C., Pandolfi, P. P., and Lin, H. K. (2010a). Deciphering the transcriptional complex critical for RhoA gene expression and cancer metastasis *Nat. Cell Biol.* 12, 457-467.
29. Suzuki M, Youle R. J., and Tjandra N (2000) structure of the BAX coregulation of dimer formation and intracellular localization. Cell: 103: 645-654.
30. Huang D C, and Strasser A. (2000). BH3 only proteins essential initiators of apoptotic cell death. Cell 103, 839-842.
31. Stephen W. G. Tait & Douglas R. Green (2010). Mitochondria and cell death: outer membrane permeabilization and beyond. *Nature Reviews Molecular Cell Biology* 11, 621-632.
32. Lin B, Kolluri S K, Lin F, Liu W, Han Y H, Cao X, Dawson M I, Reed J C, Zhang X K (2004). Conversion of Bcl-2 from protector to killer by interaction with nuclear orphan receptor Nur77/TR3. Cell. 2004 Feb. 20; 116(4): 527-40.
33. Jin Z, Gao F, Flagg T, Deng X. Tobacco-specific nitrosamine 4-(methylnitrosamino)-1-(3-pyridyl)-1-butanone promotes functional cooperation of Bcl2 and c-Myc through phosphorylation in regulating cell survival and proliferation. J Biol Chem. 2004 Sep. 17; 279(38):40209-19. Epub 2004 Jun. 21.
34. Tan Y, Demeter M R, Ruan H, Comb M J. BAD Ser-155 phosphorylation regulates BAD/Bcl-XL interaction and cell survival. J Biol Chem. 2000 Aug. 18; 275(33):25865-9.
35. Hirai I, Wang H G. Survival-factor-induced phosphorylation of Bad results in its dissociation from Bcl-x(L) but not Bcl-2. Biochem J. 2001 Oct. 15; 359 (Pt 2):345-52.
36. Datta S R, Katsov A, Hu L, Petros A, Fesik S W, Yaffe M B, Greenberg M E. 14-3-3 proteins and survival kinases cooperate to inactivate BAD by BH3 domain phosphorylation. Mol Cell. 2000 July; 6(1):41-51.
37. Hirai T, Chida K (2003). Protein kinase Czeta (PKC-zeta): activation mechanisms and cellular functions. J Biochem. January; 133(1):1-7.
39. Newton, A. C. (2001) Protein kinase C: structural and spatial regulation by phosphorylation, cofactors, and macromolecular interactions. *Chem. Rev.* 101, 2353-2364.
40. Moscat J, Diaz-Meco M T, Albert A, Campuzano S (2006). Cell signaling and function organized by PB1 domain interactions. *Mol Cell* 23:631-640.
41. Moscat J, Rennert P, Diaz-Meco M T (2006). PKC at the crossroad of NF-B and Jak1/Stat6 signaling pathways. *Cell Death Differ* 13: 702-711.
42. J Sebolt-Leopold (2000). Development of anticancer drugs targeting the MAP kinase pathway. Oncogene, 19, pp. 6594-6599.
43. K Mahadev, X Wu, H Motoshima, B J Goldstein (2004). Integration of multiple downstream signals determines the net effect of insulin on MAP kinasevs PI 3'-kinase activation: potential role of insulin-stimulated H(2)O(2). Cell Signal, 16 (2004), pp. 323-331.
44. K S M Smalley (2003). A pivotal role for ERK in the oncogenic behavior of malignant melanoma. Int J Cancer, 104, pp. 527-532.
45. R J Santen, R X Song, R McPherson, et al. The role of mitogen-activated protein (MAP) kinase in breast cancer. J Steroid Biochem Mol Biol, 80 (2002), pp. 239-256.

46. S Sato, N Fujita, T Tsuruo. Involvement of PDK1 in the MEK/MAPK signal-transduction pathway. J Biol Chem, 279 (2004), pp. 33759-33767.
47. C M Crew, A Alessandrini, R L Erikson. The primary structure of MEK, a protein kinase that phosphorylates the ERK gene product. Science, 258 (1992), pp. 478-480.
48. T S Lewis, P S Shapiro, N G Ahn. Signal transduction through MAP kinase cascades. Adv Cancer Res, 74 (1998), pp. 49-139.
49. J N Lavoie, G L'Allemain, A Brunet, et al. Cyclin D1 expression is regulated positively by the p42/p44MAPK and negatively by the p38/HOGMAPK pathway. J Biol Chem, 271 (1996), pp. 20608-20616.
50. Nicholson K. M., Anderson N. G., The Akt/PKB signaling pathway in human malignancy, *Cell signal,* 14: 381-395, 2002.
51. Hajduch E, Litherland G. J., Hundal H. S., Protein kinase B (Akt/PKB)—a key regulator of glucose transport?, *FEBS Lett.,* 492: 199-203, 2001.
52. Jones P. F., Jakubowicz T., Hemmings B. A., Molecular cloning of a second form of rac protein kinase, *Cell Regul.:* 1001-1009, 1991.
53. Cheng J. Q., Godwin A. K., Bellacosa A., Taguchi T., Franke T. F., Hamilton T. C., Tsichlis P. N., Testa J. R., AKT2, a putative oncogene encoding a member of a subfamily of protein-serine/threonine kinases, is amplified in human ovarian carcinomas, *Proc. Natl. Acad. Sci. USA.,* 89:9267-9271, 1992.
54. Brodbeck D., Cron P., Hemmings B. A., A human protein kinase B with regulatory phosphorylation sites in the activation loop and in the C-terminal hydrophobic domain, *J. Biol. Chem.,* 274: 9133-9136, 1999.
55. Lynda Elghazi, Norman Balcazar, Ernesto Bernal-Mizrachi. Emerging role of protein kinase B/Akt signaling in pancreatic beta-cell mass and function. Int J Biochem Cell Biol. 38 (2006) 689-695.
56. Juan Angel Fresno Vara, Enrique Casado, Javier de Castro, Paloma Cejas, Crist obal Belda-Iniesta, Manuel Gonzalez-Baron (2004). PIK/Akt signaling pathway and cancer. Cancer treatment review (2004) 30, 193-204.
57. Testa J R, Bellacosa A. AKT plays a central role in tumorigenesis. Proc Natl Acad Sci USA 2001; 98:10983-5.
58. Chen X, Thakkar H, Tyan F, et al. Constitutively active Akt is an important regulator of TRAIL sensitivity in prostate cancer. Oncogene 2001; 20:6073-83.
59. Kandasamy K, Srivastava R K. Role of the phosphatidylinositol 3-kinase/PTEN/Akt kinase pathway in tumor necrosis factor-related apoptosis-inducing ligand-induced apoptosis in non-small cell lung cancer cells. Cancer Res 2002; 62: 4929-37.
60. Wang Q, Wang X, Hernandez A, et al. Regulation of TRAIL expression by the phosphatidylinositol 3-kinase/Akt/GSK-3 pathway in human colon cancer cells. J Biol Chem 2002; 277:36602-10.
61. Yuan X J, Whang Y E. PTEN sensitizes prostate cancer cells to death receptor-mediated and drug-induced apoptosis through a FADD-dependent pathway. Oncogene 2002; 21:319-27.
62. http://www.cancer.org/cancer/cancerbasics/lifetime-probability-of-developing-or-dying-from-cancer.
63. http://www.cancercenter.com/colorectal-cancer/types.
64. http://www.webmd.com/colorectal-cancer/ss/slideshow-colorectal-cancer-overview.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

While there has been described and illustrated specific embodiments of the invention, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

It is also to be understood that the following claims are intended to cover all of the generic and specific features of the invention herein described, and all statements of the scope of the invention which, as a matter of language, might be said to fall there between. Now that the invention has been described,

We claim:

1. A method of treating colon cancer in a patient in need thereof comprising
    (a) selecting a patient having colon cancer cells that contain a higher level of mRNA or protein for PKC-ζ and/or PKC-ι compared to non-cancer normal colon epithelial cells, and
    (b) administering to the patient having colon cancer a therapeutically effective amount of an atypical PKC (aPKC) inhibitor selected from the group consisting of ACPD, ICA-1, DNDA, and ζ-Stat.

2. The method according to claim 1, wherein the aPKC inhibitor is ζ-Stat.

3. The method according to claim 1, wherein the subject suffers from a colon cancer that is an adenocarcinoma or a squamous cell carcinoma.

4. The method according to claim 1, wherein the colon cancer is an adenocarcinoma, a gastrointestinal carcinoid tumor, a gastrointestinal stromal tumor, a colorectal lymphoma, a colorectal non-Hodgkin lymphoma, a leiomyosarcoma, or a colorectal melanoma.

5. The method according to claim 3, wherein the squamous cell carcinoma is a primary squamous cell carcinoma or a metastasis of a squamous cell carcinoma of the esophagus or the anus.

6. A method of reducing colon cancer cell proliferation comprising
    (a) detecting a higher level of mRNA or a protein for PKC-ζ and/or PKC-ι compared to non-cancer normal colon epithelial cells, and
    (b) administering an effective amount of an atypical PKC (aPKC) inhibitor to the colon cancer cells, wherein the PKC inhibitor is selected from the group consisting of ACPD, ICA-1, DNDA, and ζ-Stat.

7. The method according to claim 6, wherein the aPKC inhibitor is ζ-Stat.

8. The method according to claim 6, wherein the colon cancer cells are from an adenocarcinoma or a squamous cell carcinoma.

9. The method of claim 1, wherein the aPKC inhibitor is ζ-Stat, and wherein the aPKC inhibitor does not inhibit PKC-ι.

10. The method of claim 6, wherein the aPKC is ζ-Stat, and wherein the ζ-stat inhibitor decreases the levels of total and phosphorylated PKC-ζ without affecting PKC-ι.

11. The method of claim 1, wherein step (a) comprises selecting a patient having colon cancer cells that contain a higher level of mRNA or protein PKC-ι compared to non-cancer normal colon epithelial cell.

* * * * *